(12) United States Patent
Elford et al.

(10) Patent No.: US 8,932,617 B2
(45) Date of Patent: *Jan. 13, 2015

(54) METHODS FOR TREATING OR PREVENTING RESTENOSIS AND OTHER VASCULAR PROLIFERATIVE DISORDERS

(76) Inventors: Howard L. Elford, Richmond, VA (US); Arturo J. Cardounel, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/234,852

(22) Filed: Sep. 16, 2011

(65) Prior Publication Data

US 2012/0329870 A1    Dec. 27, 2012

Related U.S. Application Data

(63) Continuation of application No. 11/587,706, filed as application No. PCT/US2005/014581 on Apr. 27, 2005, now Pat. No. 8,029,815.

(60) Provisional application No. 60/566,004, filed on Apr. 28, 2004.

(51) Int. Cl.
| | |
|---|---|
| A61F 13/00 | (2006.01) |
| A61F 2/00 | (2006.01) |
| A61B 5/00 | (2006.01) |
| A61K 31/625 | (2006.01) |

(52) U.S. Cl.
CPC .................................... *A61K 31/625* (2013.01)
USPC ............................ 424/422; 424/423; 600/483

(58) Field of Classification Search
None
See application file for complete search history.

(56) References Cited

U.S. PATENT DOCUMENTS

2003/0065382 A1*    4/2003    Fischell et al. ............... 623/1.15

OTHER PUBLICATIONS

Gruberg, L., 2005, Reality: Prospective, Randomized, Multicenter Head-to-Head Comparison of *Cypher* and *Taxus* Stent Systems, Presented at the American College of Cardiology Annual Scientific Session, available at www.medscape.org/viewarticle/501393_print.
Anderson HV et al. (1993) Restenosis after coronary angioplasty. J Interv Cardiol 6:187-202.
Bauters C and Isner JM (1997) The biology of rest enos is. Prog Cardiovasc Dis 40:107-116.
Bennett MR and O'Sullivan M (2001) Mechanisms of angioplasty and stent restenosis: implications for design of rational therapy. Pharmacol Ther 91 :149-166.
Bhargava Bet al. (2003) New approaches to preventing restenosis. BMJ 327:274-279.
Crook MF and Akyurek LM (2003) Gene transfer strategies to inhibit neointima formation. Trends Cardiovasc Med 13:102-106.
Drachman DE et al., (2000) Neointimal thickening after stent delivery of pac lit axel: change in composition and arrest of growth over six months. J Am Coll Cardiol 36:2325-2332.
Duilio C et al., (2001) Neutrophils are primary source of 02 radicals during reperfusion after prolonged myocardial ischemia. Am J Physiol Heart Circ Physiol 280:H2649-2657.
Elezi S et al., (1998) Vessel size and long-term outcome after coronary stent placement. Circulation 98:1875-1880.
Elford HL (1968) Effect of hydroxyurea on ribonucleotide reductase. Biochem Biophys Res Commun 33:129-135.
Elford HL, Wampler GL and van't Riet B (1979) New ribonucleotide reductase inhibitors with antineoplastic activity. Cancer Res 39:844-851.
Epstein SE et al. (1991) Cytotoxic effects of a recombinant chimeric toxin on rapidly proliferating vascular smooth muscle cells. Circulation 84:778-787.
Farb A et al. (2002) Morphological predictors of rest enos is after coronary stenting in humans. Circulation 105:2974-2980.
Fischman DL et al. (1994) A randomized comparison of coronary-stent placement and balloon angioplasty in the treatment of coronary artery disease. Stent Restenosis Study Investigators. N Engl J Med 331 :496-50 I.
Fritzer-Szekeres et al. (2000) Trimidox, an inhibitor of ribonucleotide reductase, induces apoptosis and activates caspases in HL-60 promyelocytic leukemia cells. Exp Hematol 28:924-930.
Fritzer-Szekeres et al. (1997) Iron binding capacity of didox (3,4-dihydroxybenzohydroxamie acid) and amidox (3,4-dihydroxybenzamidoxime) new inhibitors of the enzyme ribonucleotide reductase. Life Sci 61 :2231-2237.
Fritzer-Szekeres M et al. (2002) Trimidox, an inhibitor of ribonucleotide reductase, synergistically enhances the inhibition of colony formation by Ara-C in HL-60 human promyelocytic leukemia cells. Biochem Pharmacol64:481-485.
Gershlick A et al. (2004) Inhibition of restenosis with a paclitaxel-eluting, polymer-free coronary stent: the European Evaluation of Paclitaxel Eluting Stent (ELUTES) trial. Circulation 109:487-493. Epub 2004 Jan. 2026.
Goldschmidt-Clermont PJ and Moldovan L (1999) Stress, superoxide, and signal transduction. Gene Expr 7, 255-260.
Grube E et al. (2003) T AXUS 1: six- and twelve-month results from a randomized, double-blind trial on a slow-release paclitaxel-eluting stent for de novo coronary lesions. Circulation 107:38-42.
Gupta C and Yaffe SJ (1982) Phenobarbital-induced alterations in the sexual differentiation of the female rat: reversal by hydroxyurea and cycloheximide Pediatr Pharmacol (New York) 2:85-91.
Heckenkamp J, Gawenda M and. Brunkwall J (2002) Vascular restenosis. Basic science and clinical implications. J Cardiovasc Surg (Torino) 43:349-357.
Heldman A W et al. (2001) Paclitaxel stent coating inhibits neointimal hyperplasia at 4 weeks in a porcine model of coronary restenosis. Circulation 103 :2289-2295.
Horvath Z et al. (2004) Synergistic cytotoxicity of the ribonucleotide reductase inhibitor didox (3,4-dihydroxy-benzohydroxamic acid) and the alkylating agent carmustine (BCND) in 9L rat gliosarcoma cells and DAOY human medulloblastoma cells. Cancer Chemother Pharmacol. 54(2):139-45.
Inayat MS et al. (2002) Didox (a novel ribonucleotide reductase inhibitor) overcomes Bcl-2 mediated radiation resistance in prostate cancer cell line PC-3. Cancer Biol. Ther. 1:539-545.

(Continued)

*Primary Examiner* — Jeffrey T Palenik
(74) *Attorney, Agent, or Firm* — Beu Schroeder, PLLC

(57) ABSTRACT

Described herein is the use of ribonucleotide reductase inhibitors in the prevention or treatment of restenosis and other vascular proliferative disorders.

14 Claims, 9 Drawing Sheets

(56) References Cited

OTHER PUBLICATIONS

Indolfi C et al. (2003) Molecular mechanisms of in-stent restenosis and approach to therapy with eluting stents. Trends Cardiovasc Med 13:142-148.

Kastrati A et al. (2005) Sirolimus-eluting stent or paclitaxel-eluting stent vs balloon angioplasty for prevention of recurrences in patients with coronary in-stent restenosis: a randomized controlled trial. Jama, 293:165-171.

Kim JW et al. (2005) Delayed severe multivessel spasm and aborted sudden death after Taxus stent implantation. Heart 91 :e15.

Lanza GM et al. (2002) Targeted antiproliferative drug delivery to vascular smooth muscle cells with a magnetic resonance imaging nanoparticle contrast agent: implications for rational therapy of restenosis. Circulation 106:2842-2847.

Lee R et al. (1997) Selective inhibition of IζBα phosphorylation and HIV-1 LTR-directed gene expression by novel antioxidant compounds. Virology 234:277-290.

Libby P and Tanaka H (1997) The molecular bases of restenosis. Prog Cardiovasc Dis 40:97-106.

Mayhew CN et al. (2002) Short-term treatment with novel ribonucleotide reductase inhibitors Trimidox and Didox reverses late-stage murine retrovirus-induced lymphoproliferative disease with less bone marrow toxicity than hydroxyurea. Antivir Chem Chemother 13:305-314.

Mayhew CN et al. (1999) In vivo and in vitro comparison of the short-tern hematopoietic toxicity between hydroxyurea and trimidox or didox, novel ribonucleotide reductase inhibitors with potential anti-HIV-1 activity. Stem Cells 17:345-356.

Sirolimus- vs Paclitaxel-Eluting Stents in De Novo Coronary Artery Lesions the Reality Trial: A Randomized Controlled Trial, JAMA, Feb. 2006, vol. 295, No. 8, 895-904.

Natsumeda Y (1985) Purine enzymology of human colon carcinomas. Cancer Res 45:2556-2559.

Noda-Heiny H and Sobel BE (1995) Vascular smooth muscle cell migration mediated by thrombin and urokinase receptor. Am J Physiol. 1268:C1195-1201.

Pacelli R et al. (1996) Hydroxyurea reacts with heme proteins to generate nitric oxide. Lancet 347:900.

Sarkar R et al. (1997) Cell cycle effects of nitric oxide on vascular smooth muscle cells. Am J Physiol.. 272:H1810-1818.

Sarkar R and Webb RC (1998) Does nitric oxide regulate smooth muscle cell proliferation? A critical appraisal. J Vasc Res 35:135-142.

Segev A et al. (2002) Inhibition of vascular smooth muscle cell proliferation by a novel fibroblast growth factor receptor antagonist. Cardiovasc Res 53:232-241.

Shet AS et al. (2003) Sickle blood contains tissue factor-positive microparticles derived from endothelial cells and monocytes. Blood 102:2678-2683.

Sousa JE et al. (2001) Lack of neointimal proliferation after implantation of sirolimus-coated stents in human coronary arteries: a quantitative coronary angiography and three-dimensional intravascular ultrasound study. Circulation 103:192-195.

Stolze K and Nohl H (1990) EPR studies on the oxidation of hydroxyurea to paramagnetic compounds by oxyhemoglobin. Biochem Pharmacol 40:799-802.

Stone GW et al. (2004) One-year clinical results with the slow-release, polymer-based, paclitaxel-eluting TAXUS stent: the TAXUS-IV trial. Circulation 109:1942-1947.

Suzuki T et al. (2001) Stent-based delivery of sirolimus reduces neointimal formation in a porcine coronary model. Circulation 104: 1188-1193.

Takeda E and Weber G (1981) Role of ribonucleotide reductase in expression in the neoplastic program. Life Sci 28:1007-1014.

Tanaka H et al. (2000) A ribonucleotide reductase gene involved in a p53-dependent cell-cycle checkpoint for DNA damage. Nature 404:42-49.

Turchan J et al. (2003) Oxidative stress in HIV demented patients and protection ex vivo with novel antioxidants. Neurology 60:307-314.

Veda M et al. (1995) Smooth muscle cell de-differentiation is a fundamental change preceding wound healing after percutaneous trans luminal coronary angioplasty in humans. Coron Artery Dis 6:71-81.

Vaughan WP, Holm C and Cordel K (1989) Hydroxyurea potentiation of the antineoplastic activity of cyclophosphamide and 4"-(9-acridinylamino )methanesulfon-M-anisidide (AM SA) inthe brown Norway rat myelocytic leukemia model. Cancer Chemother Pharmacol., 23:26-30.

Ward MR et al. (2000) Arterial remodeling. Mechanisms and clinical implications. Circulation 102:1186-1191.

Bagshawe et al., A cytotoxic agent can be generated selectively at cancer sites (1988) Br. J. Cancer, 58:700-703.

Bagshawe, Towards generating cytotoxic agents at cancer sites (1989) Br. 1. 15 Cancer, 60:275-281.

Battelli et al., T lymphocyte killing by a xanthine-oxidase-containing immunotoxin (199~) Cancer Immunol. Immunother. 35:421-425, dated 1992.

Caplen et al. Specific inhibition of gene expression by small double-stranded RNAs in invertebrate and vertebrate systems (2001) Proc. Natl. Acad. Sci. 98:9742-9747.

Duxbilry et al., Retrovirally mediated RNA interference targeting the M2 subunit of ribonucleotide reductase: A novel therapeutic strategy in pancreatic cancer (2004) Surgery. 136(2):261-269.

Duxbury et al., RNA interference targeting the M2 subunit of ribonucleotide recuctase enhances pancreatic adenocarcinoma chemosensitivity to gemcitabine(2004) Oncogene. 23(8):1539-1548.

Elbashir et al. Duplexes of 21-nucleotide RNAs mediate RNA interference in cultured mammalian cells (2001) Nature 411 :494-8.

Gitlin et al. Short interfering RNA confers intracellular antiviral immunity in human cells (2002) Nature 418:430-4.

Letsinger et al. Cholesteryl-conjugated oligonucleotides: Synthesis, properties, and activity as inhibitors of replication of human immunodeficiency virus in cell culture. Proc Natl Acad Sci USA (1989) 86:6553-6556.

Lin et al. Stable Suppression of the R2 Subunit of Ribonucleotide Reductase by R2-targeted Short Interference RNA Sensitizes p53 (_/_) HCT-116 Colon Cancer Cells to DNA-damaging Agents and Ribonucleotide Reductase Inhibitors (2004) Biol. Chem., 279(26):27030-27038.

Pietersz et al. Antibody Conjugates for the Treatment of Cancer ( 1992) Immunolog. Reviews, 129:57-80.

Senter et al. Generation of Cytotoxic Agents by Targeted Enzymes (1993) Bioconjugate Chem., 4:3-9.

Senter et al. Generation of 5-Fluorouracil from 5-Fluorocytosine by Monoclonal Antibody-Cytosine Deaminase Conjugates (1991) Bioconjugate Chem., 2:447-451.

Agrawal et al. Cell-cycle kinetics and YSY-G pseudotyped retrovirus-mediated gene transfer in blood-derived CD34+ cells (1996) Exper. Hematol. 24:738747.

Brown et al., Molecular and Cellular Mechanisms of Receptor-Mediated Endocytosis (1991) DNA and Cell Biology 10:6, 399-409.

Brune Wolfram et al., A ribonucleotide reductase homolog of cytomegalovirus and endothelial cell tropism, Science, 2001, v. 291:5502, p. 303.

Dhananjay Kaul et al. Robust Vascular Protective Effect of Hydroxamic Acid Derivatives in a Sickle Mouse Model of Inflammation. Microcirculation. 13: 1-9,2006.

Goodman et al. Recombinant adeno-associated virus-mediated gene transfer into hematopoietic progenitor cells 25 (1994) Blood 84:1492-1500.

Henry J C et al. Inhibition of Ribonucleotide Reductase Reduces Neoiptimal Formation Following Balloon Injury, Journal of Pharmacology and Experimental Therapeutics, American Society for Pharmacology and Experimental Therapeutics. US, vol. 314, No. 1, p. 70, Feb. 2005.

Miller et al., Redesign of Retrovirus Packaging Cell Lines to Avoid Recombination Leading to Helper Virus Production (1986) Mol. Cell. Biol. .6:2895.

Mitani et al. Transduction of Human Bone Marrow by Adenoviral Vector (1994) Hum. Gene Ther. 5:941-948).

(56) References Cited

OTHER PUBLICATIONS

Naldini et al., In Vivo Gene Delivery and Stable Transduction of Nondividing Cells by a Lentiviral Vector (1996) Science 272:263267.
Pastan et al., A retrovirus carrying an MDRJ cDNA confers multidrug resistance and polarized expression of P-glycoprotein in MDCK cells (1988) Proc. Natl. Acad. Sci. U.S.A. 85:4486.
Roffler et al., Anti-neoplastic glucuronide prodrug treatment of human tumor cells targeted with a monoclonal antibody-enzyme conjugate (1991) Biochem. Pharmacol.. 42:2062-2065.
Schwartzenberger et al. Targeted gene transfer to human hematopoietic progenitor cell lines through the c-kit receptor (1996) Blood 87:472-478.
Yamauchi et al. Current systemic therapies for psoriasis: Where are we now? J. Am. Acad. Dermatol. (2003) vol. 49, No. 2, pp. 866-S77.
Beutler et al. Treatment of Multiple Sclerosis and Other Autoimmune Diseases with Cladribine, Semin Hemato133:45-52, 1996.
Campbell et al. Didox therapy for demyelinating disease, Journal of Neurochemistry, vol. 102, Aug. 6, 2007, p. 145.
Carmichael et al. A phase and I pharmacokinetic study of didox administered by 36 hour infusion, Br. J. Cancer, 61, 447-450, 1990.
Carrera et al.. Potent Toxicity of 2-Chlorodeoxyadenosine toward Human Monocytes in Vitro and in Vivo, The American Society for Clinical Investigation, Inc., vol. 86, 1480-1488, 1990.
The EP Search Report for EP08 25 2683 application dated Jun. 17, 2009.
Database CA, Chemical Abstracts Service, Columbus, Ohio, Nov. 8, 1965, Treatment of diabetes, XP002531119, Database accession No. 1967:40714.
Griffig et al. Mechanisms of Inhibition of DNA Synthesis by 2-Chlorodeoxyadenosine in Human Lymphoblastic Cells, Cancer Research, 49, 6923-6928, 1989.
Leustatin® (cladribine) Injection for Intravenous Infusion Only, Ortho Biotech Products, L.P., Raritan, NJ 08869, Aug. 2007.
Malecki et al. The case for Iron Chelation and/or Antioxidant Therapy in Alzheimer's Disease, Drug Development Res 56:526-530, 2002.
Monica Rhodes, Multiple Sclerosis (MS)—Prevention, Yahoo Health, http://heath.yahoo.com, dated Feb. 28, 2006.
Rubens et al. Phase II trial of didox in advanced breast cancer, Br. J. Cancer (1991), 64, 1187-1188.
Veale et al. A phase 1 and phannacokinetic study of didox: A ribonucleotide reductase inhibitor, Br. J. Cancer, 58, 1988.
Warnke et al. Identification of targets and new developments in the treatment of multiple sclerosis—focus on cladribine, Drug Design, Development and Therapy, 4, 117-126, 2010.
Basu, Kraddy, and Levison, Interleukin-I: A Master Regulator of Neuroinflammation 2004 Journal of Neuroscience Research, 78(2): 151-156.
Database WPI Week 199702, Treating Parkinsonian syndrome—by treatment with haloperidol at a dilution of 2:1000000, Thomson Scientific, London, GB; AN 1997-019281, XPOO2531120.
Fang et al. Hypoglycemic activity and chemical structure of the salicylates. Journal of Pharmaceutical Sciences, vol. 57, No. 12, Dec. 1968, pp. 2111-2116.
Godbout and Johnson, Age and Neuroinflammation: A Lifetime of Psychoneuroimmune Consequences 2006 Neurologic Clinics, 24(3): 521-538.
Griffin, Inflammation and neurodegenerative diseases, 2006 American Journal of Clinical Nutrition, 83(Suppl): 470S-474S.
Honig, Inflammation in Neurodegenerative Disease, 2000 Archives of Neurology, 57(6): 786-788.
Hull and Hampel, 9 Neuroinflammation in Alzheimer's Disease: Potential Targets for Disease-Modifying Drugs 2002 Ernst Schering Res Found Workshop, (39): 159-178.
Hunot and Hirsch, Neuroinflammatory Processes in Parkinson's Disease, 2003 Annals of Neurology, 53(Suppl3): S49-S58.
McGeer and McGeer, Local neuroinflammation and the progression of Alzheimer's disease, 2002 Journal of Neuroviro J., 8(6): 529-538.
Pardo et al., Immunity, neuroglia and neuroinflammation in autism, 2005 International Review of Psychiatry, 17(6): 485-495.
Vincent et al. Identification of candidate drugs for the treatment of ALS, Amyotrophic Lateral Sclerosis, London, GB, vol. 6, No. 1, Jan. 1, 2005, pp. 29-36.

Weydt and Moller, Neuroinflammation in the pathogenesis of amyotrophic lateral sclerosis, 2005 Neuroreport, 16(6):527-531.
Wyss-Coray and Mucke, Inflammation in Neurodegenerative Disease—A Double-Edged Sword, 2002 Neuron, 35: 419-432.
Bettelli et al. Reciprocal developmental pathways for the generation of pathogenic effector T H17 and regulatory T cells 2006 Nature 441: 235-238.
Chen et al. Anti-IL-23 therapy inhibits multiple inflammatory pathways and ameliorates autoimmune encephalomyelitis 2006 J. Clin. Invest. 116: 1317-1326.
Cua et al. Interleukin-23 rather than interleukin-12 is the critical cytokine for autoimmune inflammation of the brain 2003 Nature 421: 744-748.
Dorner et al. The role of B cells in rheumatoid arthritis: mechanisms and therapeutic targets 2003 Curr. Opin. Rheumatol., 15: 246-252.
Furuzawa-Carballeda et al. Autoimmune inflammation from the Th17 perspective 2007 Autoimmun Rev; 6(3):169-175.
Langrish et al. IL-23 drives a pathogenic T cell population that induces autoimmune inflammation 2005 J. Exp Med. 201: 233-240.
Molcanyi et al., Trauma-Associated Inflammatory Response Impairs Embryonic Stem Cell Survival and Integration after Implantation into Injured Rat Brain 2007 Journal of Neurotrauma, 24(4): 625-637.
Murphy et al. Divergent Pro- and Anti-inflammatory Roles for IL-23 and IL-12 in Joint Autoimmune Inflammation 2003 J. Exp Med., 198: 1951-1957.
Park et al. A distinct lineage of CD4 T cells regulates tissue inflammation by producing interleukin 172005 Nat. Immunol. 6: 1133-1141, dated 2005.
Rooker et al., Spatiotemporal Pattern of Neuroinflammation After Impact-Acceleration Closed Head Injury in the Rat, 2006 Mediators Inflammation, 2006(1): 90123.
Steinman L. A brief history of $T_H17$, the frrst major revision in the $T_H1/T_H2$ hypothesis of T cell-mediated tissue damage 2007 Nature Merl. 13, 139-145.
Takemura et al. T Cell Activation in Rheumatoid Synovium Is B Cell Dependent 2001 J Immunol., 107:4710-4718.
Tang et al., Regulatory T-cell physiology and application to treat autoimmunity 2006 Immunol Rev. 212:217-237.
Bolton, C., Recent advances in the pharmacological control of experimental allergic encephalomyelitis (EAE) and the implications for multiple sclerosis treatmentMult. Scler. 1995; 1(3); 143-9.
Database Biosis (Online) Biosciences Information Service, Philadelphia, p. 12 Jan. 2001, Brune Wolfram et al., A Ribonucleotide Reductase Homolog of Cytomegalovirus and Endothelial Cell Tropism, XP002558726.
French et al., Journal of Medicinal Chemistry, a. (N) Formylheteroaromatic Thiosemicarbazones. Inhibition of Tumor-Derived Ribonucleoside Diphosphate Reductase and Correlation with in Vivo Antitumor Activity 1974, vol. 17 (2), No. 2, p. 172.
Greenland et al., Commentary: Lifelong Prevention of Atherosclerosis: The Critical Importance of Major Risk Factor Exposures, International J. of Epidemiology, 2002, 31:1129-1134.
Henry, J. et al., Inhibition of Ribonucleotide Reductase Reduces Neointimal Formation following Balloon Injury, Journal of Pharmacology and Experimental Therapeutics, American Society of Pharmacology and Experimental Therapeutics, US, vol. 314, No. 1, Feb. 2005, pp. 70-76, XP008054477, ISSN 0022-3565.
International Preliminary Report on Patentability for PCT/US05/014581, filing date Apr. 27, 2005.
Kostulas et al. Increased IL-{beta}, IL-8, and IL-17 mRNA Expression in Blood Mononuclear Cells Observed in a Prospective Ischemic Stroke Study 1999 Stroke 10:2174-2179.
Merriam Webster Dictionary entries for the term: "prevent" and "restensis" "prevent" dated Mar. 15, 2010; "restenosis" dated Jun. 30, 2010.
Sidney Blumenthal, The American Journal of Cardiology; vol. 31, Issue 5, May 1973, pp. 591-594.
Sumpter et al., Proc Amer Assoc Cancer Res., vol. 45, 2004.
Yamauchi et al., J. Am. Acad. Dermatol., 2003, vol. 49, No. 2, pp. S66-S77.
Young et al., Hydroxyurea-induced Inhibition of Deoxyribonucleotide Synthesis: Studies in Intact Cells Cancer Res. 27 (Part 1) pp. 526-534 (1967).

\* cited by examiner

METHODS FOR TREATING OR PREVENTING RESTENOSIS AND OTHER VASCULAR PROLIFERATIVE DISORDERS

CROSS REFERENCE TO RELATED APPLICATIONS

This application is a continuation of co-pending U.S. patent application Ser. No. 11/587,706, filed Aug. 6, 2007, which is a national stage entry of International PCT Application No. PCT/US2005/014581, filed Apr. 27, 2005, which claims benefit of priority to U.S. Provisional Application No. 60/566,004, filed Apr. 28, 2004. U.S. patent application Ser. No. 11/587,706, International PCT Application No. PCT/US2005/014581 and U.S. Provisional Application No. 60/566,004 are each incorporated by reference herein in their entireties.

ACKNOWLEDGEMENTS

The research leading to this invention was funded in part by National Institute of Neurological Disorders and Stroke, Grant No. 1 R43NS044780-01A1 and the National Institutes of Health, Grants NS044780 and HL63744. The U.S. Government may have certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92719-818038.TXT, created on May 2, 2012, 4,096 bytes, machine format IBM-PC, MS-Windows operating system, is hereby incorporated by reference in its entirety for all purposes.

FIELD

Disclosed herein is the use of ribonucleotide reductase inhibitors in the prevention or treatment of restenosis or other vascular proliferative disorders.

BACKGROUND

Restenosis is the narrowing of the blood vessels, which can occur after injury to the vessel wall, for example, injury caused by surgical techniques employed to achieve revascularization. Restenosis can occur following a number of surgical procedures, for example, balloon angioplasty, transplant surgery, vein grafting, coronary by-pass grafting, and most frequently by percutaneous transluminal vascular intervention (PTVI). Unfortunately, many of these techniques are plagued by a high incidence of vessel renarrowing or restenosis. Restenosis is mediated by internal hyperplasia and is characterized by excessive proliferation of vascular smooth muscle cells in the walls of the treated blood vessel.

The vascular changes observed following PTVI involve a cascade of molecular and cellular events occurring within the vessel wall involving the release of a variety of vasoactive, thrombogenic, and mitogenic factors. These factors, acting in concert, stimulate the migration and proliferation of vascular smooth muscle cells (VSMC) and production of extracellular matrix material, which accumulate to occlude the blood vessel. Within this cascade are two processes that stand out as potential therapeutic targets; vascular remodeling and neointimal hyperplasia. Vascular remodeling, defined as any enduring change in the size and/or composition of a blood vessel, allows adaptation and repair. On the other hand, inappropriate remodeling, including its absence, underlies the pathogenesis of major cardiovascular diseases, such as atherosclerosis and restenosis. Experimental evidence acquired in vitro and in vivo suggests that the major drivers of vascular remodeling: inflammation, partially a result of oxidative stress and free radical formation; and inappropriate cell migration and proliferation are all key regulators in the remodeling process and ultimately lead to vessel restenosis.

It has been demonstrated that cytokines can trigger much of the inflammatory component of injury. Cytokines are molecules that mediate the migration of leukocytes into inflamed tissues and control the inflammatory reactions in various immune-mediated diseases. Both in animal models and in human specimens, chemokine expression is associated with atherosclerotic lesion development and vascular remodeling and restenosis after angioplasty. Activation of these inflammatory and procoagulant mechanisms is thought to contribute significantly to the initiation of restenosis. During this process, expression of tissue factor (TF) represents another one of the major physiologic triggers of coagulation that results in thrombus formation and the generation of additional signals leading to VSMC proliferation and migration.

In addition, the activity of NF-kappa B, a transcriptional regulatory factor, has been demonstrated to be involved in the inflammatory activation of endothelial cells and their adhesiveness and also appears to regulate apoptosis in smooth muscle cells (SMC) by coordinating anti-apoptotic processes. The level of activity of NF-kappa B has been shown to be enhanced within human atheromas or following angioplasty as compared with healthy vessels. Thus, the inhibition of NF-kappa B mobilization through therapeutic intervention can act to suppress endothelial activation and to induce SMC apoptosis. As mentioned, free radicals and oxidant stress also play a role in vascular pathology. Increased oxidative stress is a major characteristic of restenosis after angioplasty. The oxidative stress is mainly created by oxidants such as reactive oxygen species (ROS), which are assumed to play a role in neointima formation and smooth muscle proliferation. Once oxidant stress is invoked, characteristic pathophysiologic features follow, namely compromised vessel reactivity, vascular smooth muscle cell proliferation, macrophage adhesion, platelet activation, and lipid peroxidation, all perpetrators in the restenosis process. Evidence suggests that this complex cascade of molecular and cellular events occurring within the vessel wall culminates in cellular proliferation.

What is needed is a method of preventing or treating restenosis and other vascular proliferative disorders. The compositions and methods disclosed herein meet this and other needs.

SUMMARY

In accordance with the purposes of the disclosed materials, compounds, compositions, and methods, as embodied and broadly described herein, the disclosed subject matter, in one aspect, relates to compounds and compositions and methods for preparing and using such compounds and compositions. In another aspect, disclosed herein is the use of ribonucleotide reductase inhibitors for medical therapy in the prevention or treatment of restenosis.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF THE FIGURES

The accompanying Figures, which are incorporated in and constitute a part of this specification, illustrate several aspects and, together with the description, illustrate the disclosed compositions and methods.

FIGS. 2 A, B, and C are graphs showing the effects of Didox, Imidate, and HU on histopathological changes following balloon injury of the rat carotid artery at 2 weeks post injury. Morphometric analysis was performed at the conclusion of the study.

FIGS. 3 A, B, and C are graphs showing the effects of Didox, Imidate, and HU on histopathological changes following balloon injury of the rat carotid artery at 6 weeks post injury. Morphometric analysis was performed at the conclusion of the study.

DETAILED DESCRIPTION

Figure 1:
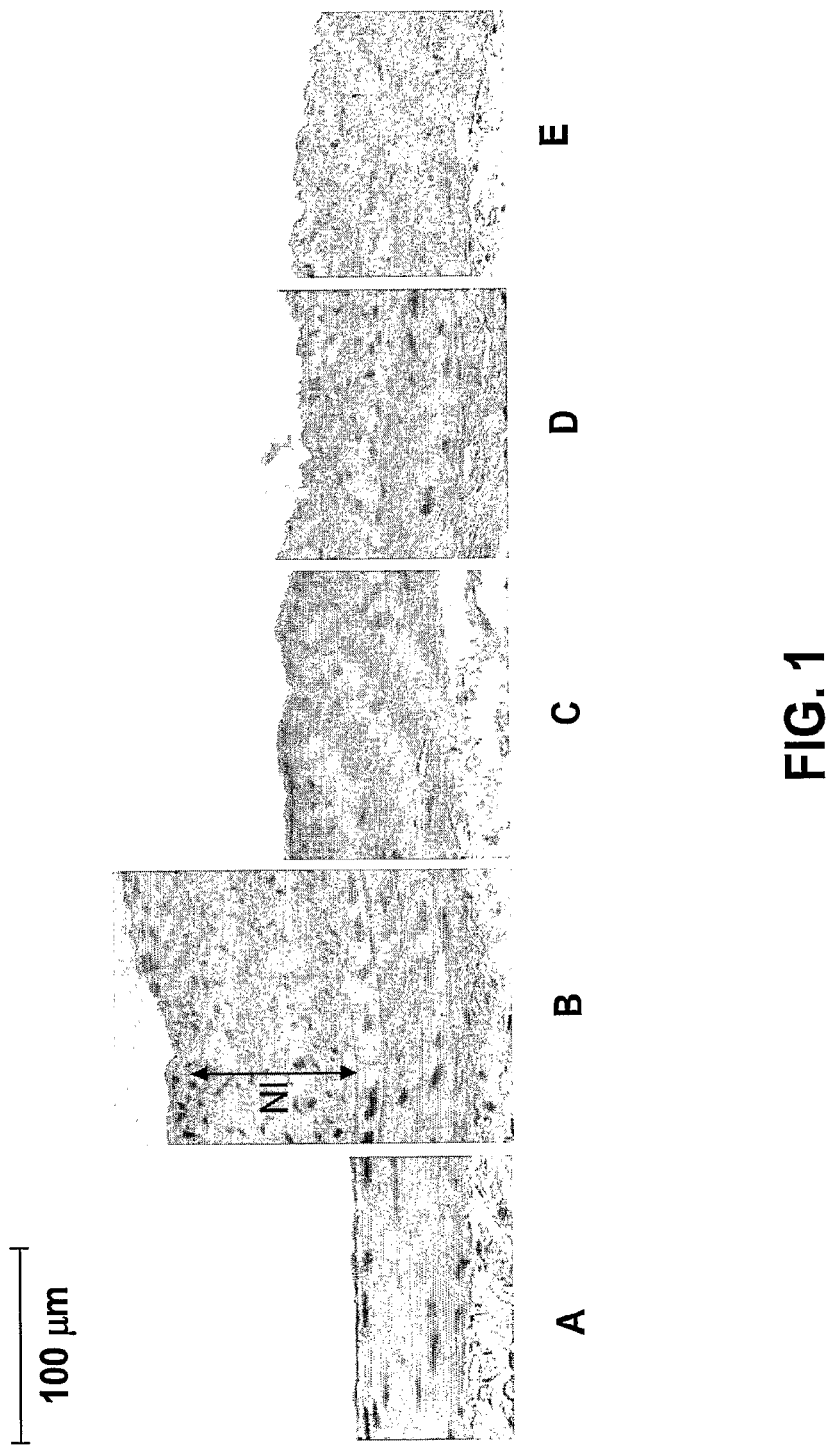
FIG. 1 is a series of photographs showing the effects of Didox, Imidate, and Hydroxyurea (HU) on the histopathology associated with balloon dilatation injury. Examples are from carotid artery sections stained with hematoxylin and eosin. Panel (A) represents a control (uninjured) section of rat carotid artery. Panel (B) demonstrates the marked neointimal hyperplasia present at 2 weeks post balloon dilatation injury. Panel (C) demonstrates the inhibitory effects of Didox (200 mg $kg^{-1}$ $d^{-1}$) on neointimal proliferation in response to balloon injury. Panel (D) demonstrates the inhibitory effects of Imidate (200 mg $kg^{-1}$ $d^{-1}$) on neointimal proliferation in response to balloon injury. Panel (E) demonstrates the inhibitory effects of HU (200 mg $kg^{-1}$ $d^{-1}$) on neointimal proliferation in response to balloon injury. Note the marked reduction in neointimal (NI) thickness following Didox, Imidate, and HU treatment.

The materials, compounds, compositions, articles, devices, and methods described herein can be understood more readily by reference to the following detailed description of specific aspects of the disclosed subject matter and the Examples included herein and to the Figures.

Before the present materials, compounds, compositions, components, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

General Definitions

In this specification and in the claims which follow, reference will be made to a number of terms which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an agent" includes mixtures of two or more such agents, reference to "the moiety" includes mixtures of two or more such moieties, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data are provided in a number of different formats, and that this data, represent endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Optional" or "optionally" means that the subsequently described event or circumstance can or cannot occur, and that the description includes instances where the event or circumstance occurs and instances where it does not.

By "inhibit" or other forms of the word such as "inhibiting" or "inhibition" is meant to hinder or restrain a particular characteristic. It is understood that this is typically in relation to some standard or expected value, in other words it is relative, but that it is not always necessary for the standard or relative value to be referred to. For example, "inhibits ribonucleotide reductase" means hindering or restraining the activity of the enzyme relative to a standard or a control. "Inhibits ribonucleotide reductase" can also mean to hinder or restrain the synthesis or expression of the enzyme relative to a standard or control.

"Treatment" or "treating" means to administer a composition to a subject or a system with an undesired condition (e.g., restenosis or other vascular proliferative disorder). The condition can include a disease. "Prevention" or "preventing" means to administer a composition to a subject or a system at risk for the condition. The condition can include a predisposition to a disease. The effect of the administration of the composition to the subject (either treating and/or preventing) can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur. It is understood that where treat or prevent are used, unless specifically indicated otherwise, the use of the other word is also expressly disclosed.

By "subject" is meant an individual. The subject can be a mammal such as a primate or a human. The term "subject" can also include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

Chemical Definitions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components or moieties of the compositions are discussed, each and every combination and permutation that are possible are specifically contemplated unless specifically indicated to the contrary. Thus, if a class of components or moieties A, B, and C are disclosed as well as a class of components or moieties D, E, and F, and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an alkyl group substituted with an aryl group can mean that the aryl group is bonded to the alkyl group via a single sigma bond and also that the aryl group and alkyl group are fused, e.g., two carbons of the alkyl group are shared with two carbons of the aryl group.

"A," "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 30 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides, e.g., fluorine, chlorine, bromine, or iodine. In another example, the term "alkylalcohol" specifically refers to an alkyl group that is substituted with one or more hydroxyl groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "acyl" refers to both unsubstituted and substituted acyl moieties, the substituted moieties can, in addition, be specifically identified herein; for example, a particular substituted acyl can be referred to as, e.g., an "acylamino" Similarly, a substituted alkoxy can be specifically referred to as, e.g., a "halogenated alkoxy," a particular substituted alkenyl can be, e.g., an "alkenylalcohol," and the like. Again, the practice of using a general term, such as "acyl," and a specific term, such as "acylamino," is not meant to imply that the general term does not also include the specific term.

The term "alkoxy" as used herein is an alkyl group bound through a single, terminal ether linkage; that is, an "alkoxy" group may be defined as —OA where A is alkyl as defined above.

The term "alkenyl" as used herein is a hydrocarbon group of from 2 to 30 carbon atoms with a structural formula containing at least one carbon-carbon double bond. Asymmetric structures such as $(A'A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol, as described below.

The term "alkynyl" as used herein is a hydrocarbon group of 2 to 30 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol, as described below.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol as described herein.

The term "cycloalkenyl" as used herein is a non-aromatic carbon-based ring composed of at least three carbon atoms and contains at least one double bound, e.g., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both.

Cyclic groups have one or more ring systems that can be substituted or unsubstituted. A cyclic group can contain one or more aryl groups, one or more non-aryl groups, or one or more aryl groups and one or more non-aryl groups.

The term "acyl" as used herein is represented by the formula A-C=O, where A can be an alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol as described herein.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "ester" as used herein is represented by the formula —OC(O)A or —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halo" as used herein refers to the halogens fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiA^1A^2A^3$, where $A^1$, $A^2$, and $A^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas —S(O)A (sulfoxide), —$S(O)_2A$ (sulfonyl), —OS$(O)_2A$ (sulfone), or —OS$(O)_2OA$, where A can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

"X," "X"," "Z," "P," "R," and "R"," where n is some integer, as used herein can, independently, possess two or more of the groups listed above. These and other specific examples are disclosed herein. For example, if R is a straight chain alkyl group, one of the hydrogen atoms of the alkyl group can optionally be substituted with a hydroxyl group (OH), an alkoxy group, halide, etc. Depending upon the groups that are selected, a first group can be incorporated within second group or, alternatively, the first group can be pendant (i.e., attached) to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Reference will now be made in detail to specific aspects of the disclosed materials, compounds, compositions, components, and methods, examples of which are illustrated in the following description and examples, and in the figures and their previous and following description.

Ribonucleotide Reductase

Disclosed herein, in one aspect, are methods of treating or preventing restenosis and other vascular proliferative disorders by administering one or more ribonucleotide reductase inhibitors. Ribonucleotide reductase catalyzes the reductive conversion of ribonucleotides to deoxynucleotides. This reductive reaction is a rate limiting step in the biochemical pathway leading to DNA synthesis and thus cell replication (Elford et al., (1970) *J Biol Chem* 245:5228-5233; Elford et al., (1979) *Cancer Res* 39:844-851; Takeda and Weber, (1981) *Life Sci* 28:1007-1014; Natsumeda et al., (1985) *Cancer Res* 45:2556-2559; Anderson et al., (1993) *J Interv Cardiol* 6:187-202; Tanaka et al., (2000) *Nature* 404:42-49). DNA synthesis cannot occur without invoking this reaction since the endogenous pools of dNTP in mammalian cells are inadequate to support new DNA synthesis (Elford et al., (1970) *J Biol Chem* 245:5228-5233; Elford et al., (1979) *Cancer Res* 39:844-851). As disclosed herein, ribonucleotide reductase is a prime target for impeding cellular proliferation, and is amenable to inhibiting VSMC replication and leukocyte production. It has been shown that rate of uncontrolled cell growth is closely associated with the specific activity of this enzyme. Because restenosis is ultimately a proliferative disease, ribonucleotide reductase inhibitors can serve as novel therapeutic agents in the treatment of restenosis following vascular trauma or injury. Also ribonucleotide reductase inhibitors can serve as novel therapeutic agents in the treatment of other disorder caused by abnormal vascular proliferation.

Ribonucleotide reductase comprises two subunits R1 and R2. The accession numbers for R1 and R2 subunits of homosapiens ribonucleotide reductase are X59617 and X59618, respectively.

Ribonucleotide Reductase Inhibitors

The ribonucleotide reductase inhibitors disclosed herein can be used for the treatment or prevention of restenosis or a vascular proliferative disorder in a subject. By "ribonucleotide reductase inhibitor" is meant any composition that impairs or inhibits the enzyme ribonucleotide reductase or any of its subunits, which, as noted herein, catalyzes the reductive reaction that converts ribonucleotides into deoxyribonucleotides. Such inhibitors can, for example, act by binding to the enzyme, preventing the enzyme from becoming active, degrade the enzyme, alter expression of the enzyme, or alter the production of the enzymer.

The reductive reaction that converts ribonucleotides into deoxyribonucleotides primarily occurs at the diphosphate form of the nucleotides. Suitable ribonucleotide reductase inhibitors can be small molecules that bind to or associate with the reductase, nucleic acid based inhibitors that reduce or prevent the expression of ribonucleotide reductase, or polypeptide based molecules that interact with the reductase to inhibit enzyme activity. Also included are deoxynucleosides that are converted in vivo to deoxynucleotide di- or tri-phosphates that interact with RR holoenzyme or it subunits to interfere with the activity of the enzyme. In one aspect, suitable examples of ribonucleotide reductase inhibitors include, but are not limited to, nucleoside inhibitors (e.g., fludarabine, 2-fluoromethylene-2' deoxycitidine-5' diphoshate, gemcitibine, 2' azido-2' deoxynucleoside of cytosine, and uracil thionucleotides), Fe-chelators (e.g., Desferrol, Desferoxamine, Desferri-Exochelin, and IC202C), thiosemicarbazides such as Triapine, small peptide inhibitors such as P7, and hydroxamic acids such as hydroxyurea. These and other ribonucleotide reductase inhibitors are described more fully herein.

Small Molecule Based Ribonucleotide Reductase Inhibitors

In one aspect, the ribonucleotide reductase inhibitors useful herein have the Formula I

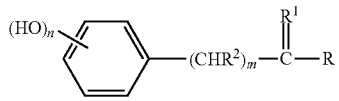

I wherein n is from 2 to 5, m is 0 or 1, R is $NH_2$, NHOH, $OC_{1-3}$ alkyl, or O-phenyl, $R^1$ is O, NH, NOH, or S and $R^2$ is H, OH, SH, or $NH_2$. It is contemplated that Formula I includes the tautomeric form where the $C=R^1$ moiety exists as a single bond ($C—R^1$), and the double bond exists in the moiety $(CR^2)_m=C$. In this tautomeric form, the variables are the same as disclosed above and further include $R^1$ being SH. In another aspect, prodrugs of the compounds having the Formula I can be used. For example, phenolic acetyl derivatives of compounds according to Formula I can be used as the ribonucleotide reductase inhibitors. In this aspect, the acetyl derivatives act as "pro-drugs" in that they are converted by the subject to the corresponding ribonucleotide reductase inhibitor having entirely unesterified phenolic hydroxyls, which are the therapeutically active drugs.

Examples of ribonucleotide reductase inhibitors covered under Formula I include, but are not limited to, 2,3-dihydroxyphenyl, 3,4-dihydroxyphenyl, 2,5-dihydroxyphenyl, 2,6-dihydroxyphenyl, 2,3,4-trihydroxyphenyl, 2,3,5-trihydroxyphenyl, 3,4,5-trihydroxyphenyl, 2,4,5-trihydroxyphenyl, 2,3,4,5-tetrahydroxyphenyl, pentahydroxyphenyl and the like groups.

In one aspect, when the ribonucleotide reductase inhibitor has the Formula I, m is 1 and $R^2$ is H (a phenylacetic acid derivative). In another aspect, when the ribonucleotide reductase inhibitor has the Formula I, m is 1 and $R^2$ is OH (a mandelic acid derivative). In a further aspect, when the ribonucleotide reductase inhibitor has the Formula I, m is 0, R is NHOH and $R^1$ is O (an N-hydroxybenzamide (formerly, a benzohydroxamic acid)). In another aspect, when the ribonucleotide reductase inhibitor has the Formula I, R is $NH_2$ and $R^1$ is NH (a benzimidamide (formerly a benzamidine)). In a further aspect, when the ribonucleotide reductase inhibitor has the Formula I, R is NHOH and $R^1$ is NH (an N-hydroxy benzimidamide (formerly a benzamidoxime)). In another aspect, when the ribonucleotide reductase inhibitor has the Formula I, R is NHOH and $R^1$ is NOH (an N,N'-dihydroxy benzimidamide (formerly, an hydroxyamidoxime)). In a further aspect, when the ribonucleotide reductase inhibitor has the Formula I, R is O-alkyl or O-phenyl and $R^1$ is NH (a benzimidate). In another aspect, when the ribonucleotide reductase inhibitor has the Formula I, R is $OC_{1-10}$ alkyl, wherein the alkyl groups include, but are not limited to, methyl, ethyl, isopropyl, and n-propyl.

Compounds represented by Formula I are disclosed in U.S. Pat. Nos. 6,248,782; 4,253,322; 4,623,659; 2,848,430 and 3,629,443, which are incorporated by reference in their entireties. Methods for their preparation are also fully disclosed in these patents as well as in the many references cited therein. In another aspect, the polyphenolic compounds N-3, 4-trihydroxybenzamide (Didox) and ethyl-3,4,5-trihydroxy-benzenecarboximidate-HCl (Imidate) can be used herein as ribonucleotide reductase inhibitors.

In another aspect, ribonucleotide reductase inhibitors having the Formula II can be used in the methods described herein

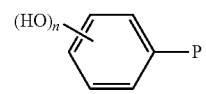

II wherein n is from 2 to 5 and P can be COOH or the pharmaceutically-acceptable salt or ester thereof, CN, $C_{1-8}$ alkyl, aryl-substituted $C_{1-8}$ alkyl, acylamino, $HOC_2H_4$—NH—$CH_2$—C(=O)—, $C_1$-$C_2H_4$—$NCH_3$—$CH_2$—C(=O)—, $C(S)OC_2H_5$, C(O)—NH—$C_{1-3}$ alkyl, C(=NH)—N(OH)—$C_{1-3}$ alkyl, and substituted variants thereof. In one aspect, phenolic blocking groups such as, for example, alkanoic acids, phenacyl esters and the like can be employed to yield pro-drugs which are removed by the subject upon administration to yield drugs containing only free phenolic hydroxyls.

In another aspect, ribonucleotide reductase inhibitors useful herein have the formula $R^3Z$, wherein $R^3$ can be H, $NH_2$, $NH_2$—NH, NHOH, NOH—$R^6$, $C_{1-6}$ alkyl, $OC_{1-6}$ alkyl, aryl-substituted with $C_{1-6}$ alkyl, phenyl, naphthyl, pyridyl, pyrimidyl or thienyl, and wherein Z can be C(=O)NOH—$R^4$, C(=S)—NOH—$R^4$, C(=NH)—NOH—$R^4$, C(=NOH)—$C_{1-3}$ alkyl, C(=NOH)—$R^4$ and C(=NOH)—$R^5$, wherein $R^4$ can be H, $C_{1-6}$ alkyl and substituted $C_{1-6}$ alkyl, wherein $R^4$ can be substituted with hydroxy, alkoxy, amino or halo, and wherein $R^5$ is $NH_2$ or NHOH, wherein $R^6$ is $C_{1-6}$ acyl, alkyl and substituted $C_{1-6}$ alkyl substituted with hydroxyl, alkoxy, amino or halo and the like. The above group of compounds are generally referred to as "hydroxyureas." The compounds disclosed in by Young, et al., (1967) *Cancer Res.* 27(Part 1):635, which is incorporated by reference in its entirety, can be used herein. In one aspect, the ribonucleotide reductase inhibitors can be hydroxyurea.

In another aspect, ribonucleotide reductase inhibitors useful in the methods herein include semithiocarbazones such as, for example, 2-formylpyridine, 2-acetylpyridine, 1-formylisoquinoline, 1-acetylisoquinoline, and their ring substituted analogs. Formulae III and IV below illustrate these compounds

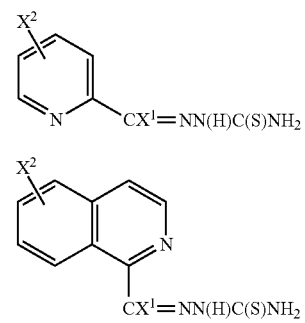

wherein Formula III represents pyridine-type compounds and Formula IV represents isoquinoline-semithiocarbazones, where $X^1$ can be H or $CH_3$, $X^2$ can be H, OH, $NH_2$, F, $CF_3$, $C_{1-3}$ alkyl, $OX^3$, $NHX^3N(X^3)_2$, and $O(O=C)X^4$, in which $X^3$ denotes $C_{1-3}$ alkyl and $X^4$ can be aryl, $C_{1-6}$ alkyl including substitutions on the alkyl chain of the carboxylic acid with $C_{1-3}$ alkoxy, $C_{1-3}$ mono- or di-alkylamino, aryloxy, also those in which the aryl ring is substituted with one or more hydroxy, amino or chloro groups. Both E and Z isomers of the compounds and their mixtures can be used herein.

In one aspect, 2-formylpyridine and 2-acetylpyridine thiosemicarbazone derivatives useful herein include 3-hydroxy, 3-amino, 3-methyl, 3-methoxy, 3-acetoxy, 3-ethoxy, 3-fluoro, 5-hydroxy, 5-amino, 5-fluoro, 5-trifluoromethyl, 5-methoxy, 5-ethoxy, 5-dimethylamino, 5-pivaloyloxy, 5-phenoxyacetoxy, 5-N,N-dimethylaminoacetoxy, and 3,4-dihydroxybenzoyloxy as ring substituents. In another aspect, 1-formylisoquinoline and 1-acetylisoquinoline thiosemicarbazone derivatives useful herein include 4-hydroxy, 4-methyl, 4-amino, 5-fluoro, 5-trifluoromethyl, 5-amino and 5-acetylamino as ring substituents. The 2-formylpyridine and 1-formylisoquinoline thiosemicarbazone derivatives disclosed in French et al, (1974) *J Med Chem* 17:172, which is incorporated by reference in its entirety, can be used herein. Other examples of thiosemicarbazone derivatives that can be used in the compositions and methods disclosed herein are described in U.S. Pat. Nos. 5,869,676, and 5,767,134, which are incorporated by reference herein for at least their teachings of thiosemicarbazone derivatives.

Still other examples of small molecule ribonucleotide reductase inhibitors that can be used in the disclosed compositions and methods are disclosed in U.S. Pat. Nos. 5,760,210, 5,569,666, 5,589,587, 5,550,144, 5,545,650, 5,545,649, 5,541,207, 5,536,739, 5,536,738, 5,519,041, 5,514,695, 5,508,393, 5,498,622, 5,496,841, 5,496,840, 5,496,839, 5,496,838, 5,496,837, 5,476,841, 5,466,702, 5,391,563, 5,292,775, 5,198,425, 5,173,505, 5,128,353, 5,071,835, 4,845,195, 4,837,304, 4,814,432, which are incorporated by reference herein for at least their teachings of ribonucleotide reductase inhibitors.

Nucleic Acid Based Inhibitors

In another aspect, a suitable ribonucleotide reductase inhibitor can be a nucleic acid based inhibitor. There are a variety of molecules disclosed herein that are nucleic acid based. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenine-9-yl (A), cytosine-1-yl (C), guanine-9-yl (G), uracil-1-yl (U), and thymine-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc Natl Acad Sci USA* (1989) 86:6553-6556).

Antisense

Antisense molecules are one example of suitable nucleic acid based ribonucleotide reductase inhibitors that can be used in the disclosed methods and compositions. Antisense molecules are designed to interact with a target nucleic acid molecule through either canonical or non-canonical base pairing. The interaction of the antisense molecule and the target molecule (e.g., ribonucleotide reductase or a subunit thereof) is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

To design antisense oligonucleotides, a host mRNA sequence is examined. Regions of the sequence containing multiple repeats, such as TTTTTTTT, are not as desirable because they will lack specificity. Several different regions can be chosen. Of those, oligonucleotides are selected by the following characteristics: those having the best conformation in solution; those optimized for hybridization characteristics; and those having less potential to form secondary structures. Antisense molecules having a propensity to generate secondary structures are less desirable.

Suitable antisense molecules for the disclosed methods and compositions impair ribonucleotide reductase synthesis or activity. Antisense molecules that can be used in the disclosed methods and compositions can also be obtained commercially. For example, Lorus Therapeutics (Toronto, Canada) has developed antisense molecules which are specific for either R1 or R2 mRNA, the two subunits of ribonucleotide reductase. Specific examples of antisense molecules from Lorus that can be used in the disclosed methods and compositions include GTI-2040 and GTI-2501. Recent toxicology studies with rodents and monkeys have indicated that this compound is likely to be safe in humans at concentrations that exceed therapeutic doses. GTI-2040 (having following sequence 5'-GGCTAAATCGCTCCACCAAG-3' (SEQ ID NO:1)) is currently in a Phase II clinical trial for patients with advanced or metastatic renal cell carcinoma. GTI-2501 is in Phase II clinical trials for use in hormone-refractory prostate cancer in combination with docetaxel. Other examples of suitable antisense molecules that can be used in the disclosed methods and compositions are disclosed in U.S. Pat. Nos. 6,593,305, 6,121,000, and 5,998,383, which are incorporated by reference herein in for at least their teachings of antisense ribonucleotide reductase inhibitors.

Short Interfering RNAs

Short interfering RNAs (siRNAs) are another example of suitable nucleic acid based ribonucleotide reductase inhibitors that can be used in the disclosed methods and compositions. siRNAs are double-stranded RNAs that can induce sequence-specific post-transcriptional gene silencing, thereby decreasing or even inhibiting gene expression.

In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends. The direction of dsRNA processing determines whether a sense or an antisense target RNA can be cleaved by the produced siRNA endonuclease complex. Thus, siRNAs can be used to modulate transcription, for example, by silencing genes, such as B-chimerin rho-GTPase or Rab9. The effects of siRNAs have been demonstrated in cells from a variety of organisms, including *Drosophila, C. elegans*, insects, frogs, plants, fungi, mice and humans (for example, WO 02/44321; Gitlin et al., (2002) *Nature* 418:430-4; Caplen et al., (2001) *Proc. Natl. Acad. Sci.* 98:9742-9747; and Elbashir et al., (2001) *Nature* 411:494-8). In certain examples, siRNAs are directed against certain target genes, such as ribonucleotide reductase.

Examples of siRNA that can be used to inhibit the expression of ribonucleotide reductase, as disclosed herein, are disclosed in Duxbury et al., (2004) Oncogene. 23(8):1539-1548; Duxbury et al., (2004) Surgery. 136(2):261-269; Lin et al., (2004) *Biol. Chem.*, 279(26):27030-27038; which are incorporated by reference herein for at least their teachings of siRNA.

Polypeptide Based Ribonucleotide Reductase Inhibitors

In yet another aspect, a suitable ribonucleotide reductase inhibitor can be a polypeptide (for example, an antibody specific for ribonucleotide reductase or subunits R1, R2, or p53 thereof). Examples of polypeptide based ribonucleotide reductase inhibitors are disclosed in U.S. Pat. Nos. 6,030,942 and 5,885,830, which are incorporated by reference herein for at least their teachings of polypeptide based ribonucleotide inhibitors. In one example, P7 is a suitable peptide based ribonucleotide reductase inhibitor having the sequence TLDADF (SEQ ID NO:2). P7 corresponds to the C-terminus of mR2 and competes with mR2 for binding to mR1.

Pharmaceutically Acceptable Salts

Where possible, any of the compounds described herein can be the pharmaceutically acceptable salt or ester thereof. In one aspect, pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of ribonucleotide reductase inhibitor to base used is chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

Some of the ribonucleotide reductase inhibitors may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines. In another aspect, the ribonucleotide reductase inhibitor is in the form of the sodium or potassium salt. In another embodiment, the ribonucleotide reductase inhibitors can be converted to the corresponding pharmaceutically-acceptable ester such as, for example, the methyl ester.

Methods of Use

The disclosed ribonucleotide reductase inhibitors have a wide variety of uses, for example, they can be used to treat or prevent restenosis or other vascular proliferative disorders following injury or various surgical procedures.

As an example, the disclosed ribonucleotide reductase inhibitors can be used to treat or prevent restenosis and other vascular proliferation disorders in a subject in need thereof. In one aspect, a subject can be identified as being at risk for restenosis or other vascular proliferation disorders. Subjects at risk for restenosis are generally those who have undergone or are undergoing a vascular trauma, for example, following percutaneous transluminal coronary angioplasty (PTCA). The use of PTCA has greatly reduced the number of fatalities in patients who suffer myocardial infarction (Fischman et al., (1994) *N Engl J Med* 331:496-501; Elezi et al., (1998) *Circulation* 98:1875-1880; Bennett and O'Sullivan, (2001) *Pharmacol Ther* 91:149-166). During PTCA, the artery walls are expanded by several times their original diameter in an attempt to increase lumen diameter and improve flow. Unfortunately, this technique is plagued by a high incidence of vessel renarrowing or restenosis occurring in 30-40% of patients within 6 months of the procedure (Anderson et al., (1993). *J Interv Cardiol* 6:187-202; Fischman et al., (1994) *N Engl J Med* 331:496-501; Elezi et al., (1998) *Circulation* 98:1875-1880; Bennett and O'Sullivan, (2001) *Pharmacol Ther* 91:149-166; Heckenkamp et al., (2002) *J Cardiovasc*

*Surg (Torino)* 43:349-357). Prevention of restenosis after successful PTCA remains one of the most challenging tasks in the treatment of obstructive coronary artery disease. Attempts to ameliorate this proliferative response involve the use coronary stents, which have significantly improved both short term and long term outcome following interventional coronary revascularization procedures. Despite a reduction in restenosis rate with stent deployment, restenosis still occurs in 15-30% of patients within 6 months (Fischman et al., (1994) *N Engl J Med* 331:496-501; Elezi et al., (1998) *Circulation* 98:1875-1880). This incidence of in-stent restenosis is expected to increase as coronary stenting is becoming more frequent and is used in less ideal lesions. Therefore, in addition to mechanical intervention, pharmacological approaches to reduce the incidence and degree of restenosis, such as those disclosed herein, are needed.

The vascular trauma associated with PTCA involves a cascade of molecular and cellular events occurring within the vessel wall involving the release of a variety of vasoactive, thrombogenic, and mitogenic factors (Bauters and Isner, (1997) *Frog Cardiovasc Dis* 40:107-116; Libby and Tanaka, (1997) *Prog Cardiovasc Dis* 40:97-106; Goldschmidt-Clermont and Moldovan, (1999) *Gene Expr* 7:255-260). Within this cascade, several mechanisms contribute to restenosis including elastic recoil, thrombosis, smooth muscle cell migration/proliferation and matrix formation. The result of these vascular events is intimal hyperplasia, whereby vascular smooth muscle cells (VSMC's) migrate from the media to the intima, proliferate, and consequently form the neointima. During this proliferative response, SMCs undergo a phenotypic modulation from a contractile to a synthetic phenotype (differentiation) (Epstein et al., (1991) *Circulation* 84:778-787; Noda-Heiny and Sobel, (1995) *Am J Physiol* 268: C1195-1201; Ueda et al., (1995) *Coron Artery Dis* 6:71-81; Farb et al., (2002) *Circulation* 105:2974-2980; Indolfi et al., (2003) *Trends Cardiovasc Med* 13:142-148). While not wishing to be bound by theory, the compounds and compositions are believed to be effective because they target/impede smooth muscle cell migration and cell proliferation, critical components of restenosis injury. Thus, the disclose ribonucleotide reductase inhibitors can be used to treat or prevent restenosis and other vascular proliferative disorders.

i. Delivery

As used throughout, administration of any of the ribonucleotide reductase inhibitors described herein can occur in conjunction with other therapeutic agents. Thus, the ribonucleotide reductase inhibitors can be administered alone or in combination with one or more therapeutic agents. For example, a subject can be treated with a ribonucleotide reductase inhibitor alone, or in combination with chemotherapeutic agents, antibodies, antibiotics, antivirals, steroidal and non-steroidal anti-inflammatories, conventional immunotherapeutic agents, cytokines, chemokines and/or growth factors. Combinations can be administered either concomitantly (e.g., as an admixture), separately but simultaneously (e.g., via separate intravenous lines into the same subject), or sequentially (e.g., one of the compounds or agents is given first followed by the second). Thus, the term "combination" or "combined" is used to refer to either concomitant, simultaneous, or sequential administration of two or more agents. In one aspect, the ribonucleotide reductase inhibitors can be combined with other agents such as, for example, Paclitaxel, Taxotere, other taxoid compounds, other anti proliferative agents such as Methotrexate, anthracyclines such as doxorubicin, immunosuppressive agents such as Everolimus and Serolimus, and other rapamycin and rapamycin derivatives.

The ribonucleotide reductase inhibitors can be administered in a number of ways depending on whether local or systemic treatment is desired, and on the area to be treated. Administration can be topically (including opthamalically, vaginally, rectally, intranasally), orally, by inhalation, or parenterally, for example by intravenous drip, subcutaneous, intraperitoneal or intramuscular injection. The disclosed compounds can be administered intravenously, intraarterialy, intraperitoneally, intramuscularly, subcutaneously, intracavity, transdermally, intratracheal, extracorporeally, or topically (e.g., topical intranasal administration or administration by inhalant). As used herein, "topical intranasal administration" means delivery of the compositions into the nose and nasal passages through one or both of the nares and can comprise delivery by a spraying mechanism or droplet mechanism, or through aerosolization of the ribonucleotide inhibitor or mendicant. The latter can be effective when a large number of subjects are to be treated simultaneously. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety for the methods taught.

The compositions can be in solution or in suspension (for example, incorporated into microparticles, liposomes, or cells). These compositions can be targeted to a particular cell type via antibodies, receptors, or receptor ligands. The following references are examples of the use of this technology to target specific proteins to given tissue (Senter et al., (1991) *Bioconjugate Chem.*, 2:447-451; Bagshawe, (1989) *Br. J. Cancer*, 60:275-281; Bagshawe et al., (1988) *Br. J. Cancer*, 58:700-703; Senter et al., (1993) *Bioconjugate Chem.*, 4:3-9; Battelli et al., (1992) *Cancer Immunol. Immunother.* 35:421-425; Pietersz and McKenzie, (1992) *Immunolog. Reviews*, 129:57-80; Roffler et al., (1991) *Biochem. Pharmacol.*, 42:2062-2065). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, (1991) *DNA and Cell Biology* 10:6, 399-409).

When nucleic acid based ribonucleotide inhibitors are used in the disclosed methods, these compositions can be administrated and taken up into the cells of a subject (i.e., gene transduction or transfection) in the form of naked DNA or RNA, or the nucleic acids can be in a vector for delivering the nucleic acids to the cells, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., (1988) *Proc. Natl. Acad. Sci. U.S.A.* 85:4486; Miller et al., (1986) *Mol. Cell. Biol.* 6:2895). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Milani et al., (1994) *Hum. Gene Ther.* 5:941-948), adeno-associated viral (AAV) vectors (Goodman et al., (1994) *Blood* 84:1492-1500), lentiviral vectors (Naidini et al., (1996) *Science* 272:263-267), pseudotyped retroviral vectors (Agrawal et al., (1996) *Exper. Hematol.* 24:738-747). Physical transduction techniques can also be used, such as liposome delivery and receptor-mediated and other endocytosis mechanisms (see, for example, Schwartzenberger et al., (1996) *Blood* 87:472-478). This disclosed compositions and methods can be used in conjunction with any of these or other commonly used gene transfer methods.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Amounts

As disclosed herein, the ribonucleotide reductase inhibitors are administered to a subject in an effective amount. By "effective amount" is meant a therapeutic amount needed to achieve the desired result or results, e.g., treating or preventing restenosis or other vascular proliferation disorders. The exact amount of the compositions required will vary from subject to subject, depending on the species, age, weight and general condition of the subject, the severity of the disorder being treated, its mode of administration and the like. Thus, it is not possible to specify an exact amount for every composition. However, an appropriate amount can be determined by one of ordinary skill in the art using only routine experimentation given the teachings herein.

ii. Pharmaceutically Acceptable Carriers

The ribonucleotide reductase inhibitors can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

In one aspect, any of the ribonucleotide reductase inhibitors described herein can be combined with at least one pharmaceutically-acceptable carrier to produce a pharmaceutical composition. The pharmaceutical compositions can be prepared using techniques known in the art. In one aspect, the composition is prepared by admixing the ribonucleotide reductase inhibitor having with a pharmaceutically-acceptable carrier. The term "admixing" is defined as mixing the two components together so that there is no chemical reaction or physical interaction. The term "admixing" also includes the chemical reaction or physical interaction between the ribonucleotide reductase inhibitor and the pharmaceutically-acceptable carrier.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

iii. Therapeutic Uses

In one aspect, disclosed are methods for treating or preventing restenosis and other vascular proliferation disorders in a subject, comprising administering to the subject an effective amount of a ribonucleotide reductase inhibitor. In one aspect, ribonucleotide reductase inhibitors can be used for the treatment of restenosis injury following a number of surgical techniques including, but not limited to, transplant surgery, vein grafting, coronary by-pass grafting, PTCA, and angioplasty.

In other aspects, ribonucleotide reductase inhibitors can be used for the treatment of benign vascular proliferative disorders. Examples of such disorders include, but are not limited to, vascular proliferation involved in atherosclerosis, vascular proliferation following intravascular device implantation, vascular proliferation at the site of vascular anastamosis as generally occurs following revascularization procedure or A-V shunting, vascular proliferation following carotid endarderectomy, and transplant vasculopathy.

Not wishing to be bound by theory, it is believed that ribonucleotide reductase inhibitors possess chemical and biological properties that can impair several processes that contribute to the restenosis process or other vascular proliferative disorders. For example, members of the polyphenolic series such as 3,4-dihydroxy- and 3,4,5-trihydroxy-compounds have been shown to be good anti-inflammatory agents by inhibiting NF-kappa B activation and, therefore, down regulating cytokines contributing to the inflammation process and chemoattractant production. Also these compounds can inhibit tissue factor production. This synergistic concept can be a vasoprotective approach to the prevention of restenosis or other vascular proliferation disorders by attenuating inflammatory reactions, SMC proliferation, and neointima formation following vascular injury.

In one aspect, polyhydroxy phenolic compounds described herein have the ability to modulate several of the biological events contributing to the development of restenosis, uncontrolled SMC proliferation, leukocyte migration, NF-kappa B activation and tissue factor expression, leading to inflammation. These compounds being excellent free-radical scavengers, are able to modulate the above mentioned deleterious processes. Having these properties make these compounds unique to limit the restenosis process or other vascular proliferation disorders.

In one aspect, a medical device can comprise one or more ribonucleotide reductase inhibitors in order to treat or prevent restenosis or other vascular proliferation disorders. In one aspect, an implant of a medical device such as, for example, a stent, can contain the ribonucleotide reductase inhibitor. In other examples, the medical device can be a needle, cannula, catheter, shunt, balloon, or valve. The ribonucleotide reductase inhibitor can be formulated to permit its incorporation onto the medical device, which can apply the ribonucleotide reductase inhibitor directly to the site to prevent or treat such restenosis or other vascular proliferation disorder. In one aspect, the ribonucleotide reductase inhibitor can be formulated by including it within a coating on the medical device. There are various coatings that can be utilized such as, for example, polymer coatings that can release the ribonucleotide reductase inhibitor over a prescribed time period. In another aspect, the ribonucleotide reductase inhibitor can be embedded directly into the medical device.

In another aspect, the ribonucleotide reductase inhibitors can play a further positive role in preventing restenosis in organ transplantation or other surgical procedures where the incidence of viral infection is possible. Examples of viral infections include, but are not limited to, Herpes viruses, particularly cytomegalovirus, herpes I and II, hepatitis B and C, as well as HIV I and II. Viral infections can contribute to the restenosis process caused by the surgical vascular procedures listed above. Therefore, in this aspect, the ribonucleotide reductase inhibitors can prevent restenosis by inhibiting viruses such as herpes and HIV replication and the possible inflammatory aspect of hepatitis C that contribute to restenosis.

EXAMPLES

The following example is put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

The following examples test the ability of three ribonucleotide reductase inhibitors to limit the degree of restenosis following balloon mediated dilatation injury in the rat. Specifically, the ability of the polyhydroxy-phenolic compounds, Didox (3,4-dihydroxybenzohydraxamic acid), Imidate (3,4,5-hydroxybenzimidate), and hydroxyurea have been examined to limit the degree of restenosis following vascular injury.

Example 1

To determine the ability of the ribonucleotide reductase inhibitors to affect restenosis, a rat model of balloon mediated carotid artery injury was utilized. Percutaneous transluminal carotid angioplasty (PTCA) was performed using a 2F Fogarty Embolectomy Catheter, which was inserted through the right, external carotid artery and inflated (2 atm) and deflated four times inside the right common carotid artery and rotated to cause endothelial injury. Immediately following the carotid injury, the rats received ribonucleotide reductase inhibitors, Didox (N,3,4-trihydroxybenzamide) Imidate (ethyl-3,4,5-trihydroxybenzenecarboximidate.HCl), or Hydroxyurea via intraperitoneal injection. The degree of restenosis was assessed using morphometric analysis at two weeks post injury. For example, ribonucleotide reductase inhibition with Didox resulted in a 19% increase in lumen area, 84% decrease in neointimal formation, 48% reduction in total wall thickness and an 85% reduction in the intima/media ratio as compared to the untreated injured artery (Table 1). These results suggest that ribonucleotide reductase does serve as a novel therapeutic target in the treatment of post PTCA restenosis.

TABLE 1

Effects of Ribonucleotide Reductase Inhibitors on Restenosis-Data presented as % change as compared to injured vessel.

| Group | Lumen | Neointima | Wall Thickness | Neointima/Media |
|---|---|---|---|---|
| Didox | ↑19 ± 3% | ↓ 84 ± 2% | ↓ 48 ± 3% | ↓ 85 ± 4% |
| Imidate | ↑19 ± 5% | ↓ 65 ± 7% | ↓ 41 ± 7% | ↓ 69 ± 8% |
| Hydroxyurea | ↑22 ± 5% | ↓ 91 ± 6% | ↓ 54 ± 9% | ↓ 93 ± 7% |

Example 2

Didox, Imidate, and Hydroxyurea were provided by Molecules for Health Inc. (Richmond, Va.). Rat vascular smooth muscle cells and culture media were purchased from ATCC (Manassas, Va.). Fogarty embolectomy catheters were purchased from M & I medical (Miami, Fl.). All other reagents were purchased from Sigma Chemical Co. (St. Louis, Mo.).

Carotid Injury

Male Wistar rats, weighing 400-450 g (Harlan) were fed standard pellet feed and given water ad libitum. The experimental protocol was designed in accordance with Institutional ILACUC standards. Animals were anesthetized with Isoflurane (1.5-2%) in air. The right carotid artery was exposed and a 2F Fogarty balloon embolectomy catheter (Baxter) was inserted via an external carotid arteriotomy incision. The catheter was advanced to the common carotid artery, inflated to a pressure of 2 atm and rotated in a forward and retrograde direction. The catheter was then deflated and the process repeated three times. Treatment cohorts were divided into 5 groups (n=6-8/group): Control (sham operated), Didox (200 mg-kg$^{-1}$ d$^{-1}$), Imidate (200 mg kg$^{-1}$)HU (200 mg kg$^{-1}$ d$^{-1}$) and vehicle (saline). Drugs were administered daily by i.p. injection for a period of 7 days after injury. At 2 weeks post-injury, rats were euthanized by pentobarbital overdose and perfused with 10% buffered formalin Carotid arteries were removed and placed in the same fixative. Tissues were then embedded in paraffin, and 4 to 5 sections (4 μm) were cut at multiple levels. These sections were then stained with hematoxylin-eosin or elastic-van Gieson stain. Sections were examined microscopically and the cross-sectional areas of the lumen, neointima (from the internal elastic lamina to the lumen), and media were determined using digital microscopy with Spot Advanced software. The intima-to-media (I/M) ratio was then calculated from the determined mean. The data represent the mean±SD.

Flow Cytometry

SMC were plated on 6 well dishes at a density of 2×10$^5$ cells per well. Cells were then treated with Didox (0-200 μM), Imidate (0-200 μM) or HU (0-1000 μM) and incubated for 24 hours. Following the 24 hour incubation period, the cells were trypsinized and collected in 15 mL centrifuge tubes. The cells were then centrifuged 5 minutes at 800×g. The supernatant was discarded and the pellet was resuspended in 5 ml PBS. The cells were centrifuged 6 minutes at 200×g. The supernatant was removed and the pellet was then thoroughly resuspended in 0.5 ml PBS. The cell suspension was transferred into tubes containing 70% ethanol, keeping the cells in fixative for greater than about 2 hours. The ethanol suspended cells were centrifuged 5 minutes at 200×g, and the ethanol was decanted. The cell pellet was resuspended in 5 ml PBS and after one minute was centrifuged 5 min at 200×g. The top layer of liquid was again removed and the cell pellet was resuspended in 1 ml PI/Triton X-100 staining solution with RNAse A. This staining solution was then incubated at room temperature for 30 minutes. Flow cytometry was then performed using a FACS Calibur (Becton Dickenson). The data are presented as the mean.

Intracellular dNTP Quantitation

SMC were plated in T150 flasks and treated with Didox (0-200 μM), Imidate (0-200 μM) or HU (0-1000 μM) and incubated for 24 hours. Following the 24 hour incubation period, the cells were trypsinized and collected in 50 mL centrifuge tubes along with the incubation media. All the extraction steps were performed on ice. Immediately before processing, cells were counted and viability determined using the trypan blue exclusion method. The cells were then centrifuged 5 minutes at 800×g. The cell pellet was then deproteinized with the same volume of 6% TCA, vortexed for 20 s and incubated on ice for 10 minutes. The acid cell extracts were centrifuged 10 min at 2000×g. The supernatants were then supplemented with an equal volume of distilled water, vortexed for 60 s and neutralized by the addition of 5M K$_2$CO$_3$ prior to HPLC analysis. dNTP detection was carried out using an ESA (Chelmsford, Mass.) HPLC chromatographic system with UV-Vis detection. Chromatographic separations were performed using a TosoHaas C18 reverse phase column (ODS 80Tm 250×4.6 mm, 5 μm pore). The mobile phase was delivered at a rate of 1.0 mL/min during the analysis using the following stepwise gradient elution program: A-B (80-20) at 0 min; (40-60) at 30 min; (40-60) at 40 min and (80-20) at 45 min. Buffer A contained 10 mM tetrabutylammonium sulfate, 10 mM KH$_2$PO$_4$ and 0.25% MeOH, and adjusted to pH 6.9. Buffer B consisted of 5.6 mM tetrabutylammonium sulfate, 50 mM KH$_2$PO$_4$ and 30% MeOH, and neutralized to pH 7.0. The injection volume for analysis was 50 μL. Detection was carried out at 254 nm.

Smooth Muscle Cell Migration

A wound scrape assay was performed using rat vascular SMC. The cells were grown to confluence on 60 mm dishes. The cells were then made quiescent by incubating them in media containing 0.1% serum for 24 hrs followed by treatment with Didox, Imidate (0-100 μM), or HU (0-1000 μM) in media containing 0.1% serum and platelet derived growth factor (PDGF) at concentration of 10 ng/mL. Linear wounds were made by scraping each plate with the tip of a 20 μL pipette. The ability of cells to migrate across the wound area was measured using digital microscopy. SPOT advanced software (Diagnostic Instruments, Inc., Sterling Heights, Mich.) was used to measure the wound immediately, 2, 4, 12 and 24 hrs following injury. The data are presented as rate of migration and represent the mean±SD.

Results: Effects of Ribonucleotide Reductase Inhibitors on Restenosis Following Vascular Injury The effects of Didox, Imidate, and Hydroxyurea (HU) on the vascular remodeling process following arterial injury were determined using a rat model of balloon mediated carotid injury. Each compound (200 mg kg$^{-1}$ d$^{-1}$) was delivered via i.p. injection for a period of 7 days post injury. These dosages are based on previously published reports and represent ½ the maximum tolerated dose of Hydroyurea in rats (Gupta and Yaffe, (1982) *Pediatr Pharmacol (New York)* 2:85-91; Vaughan et al., (1989) *Cancer Chemother Pharmacol* 23:26-30). Furthermore, it has previously been demonstrated that these doses are sufficient to inhibit ribonucleotide reductase activity without causing significant toxicity in mice and rats (Mayhew et al., (2002) *Antivir Chem Chemother* 13:305-314; Mayhew et al., (1999) *Stem Cells* 17:345-356; Horvath et al., (2004) *Cancer Chemother Pharmacol.* 54(2): 139-145).

Figure 2A:
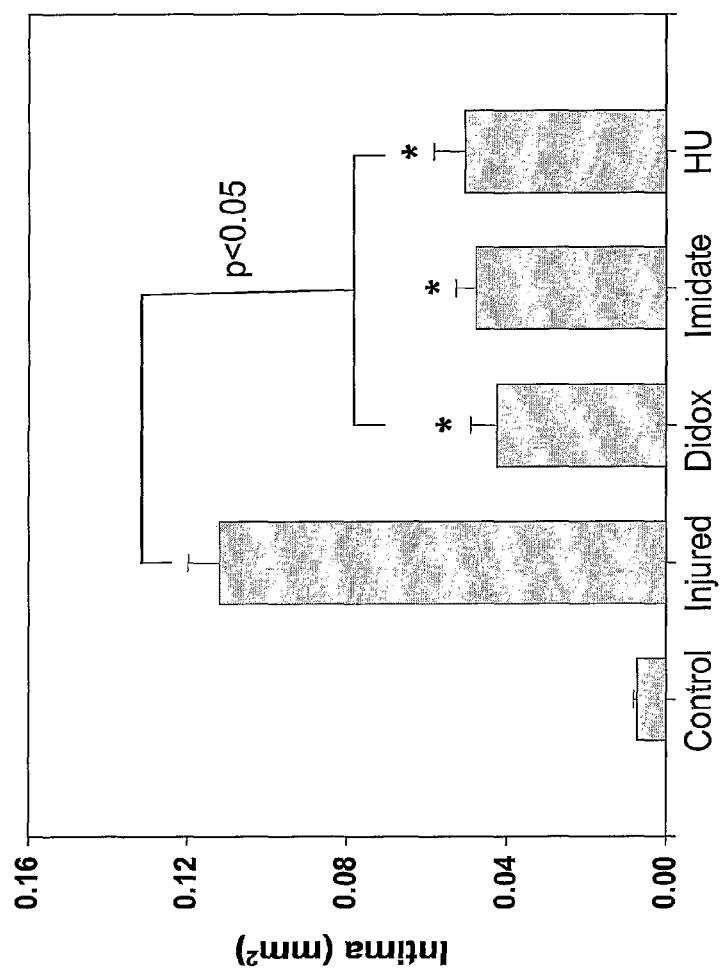
FIG. 2A compares neointima formation ($mm^2$).
Figure 2B:
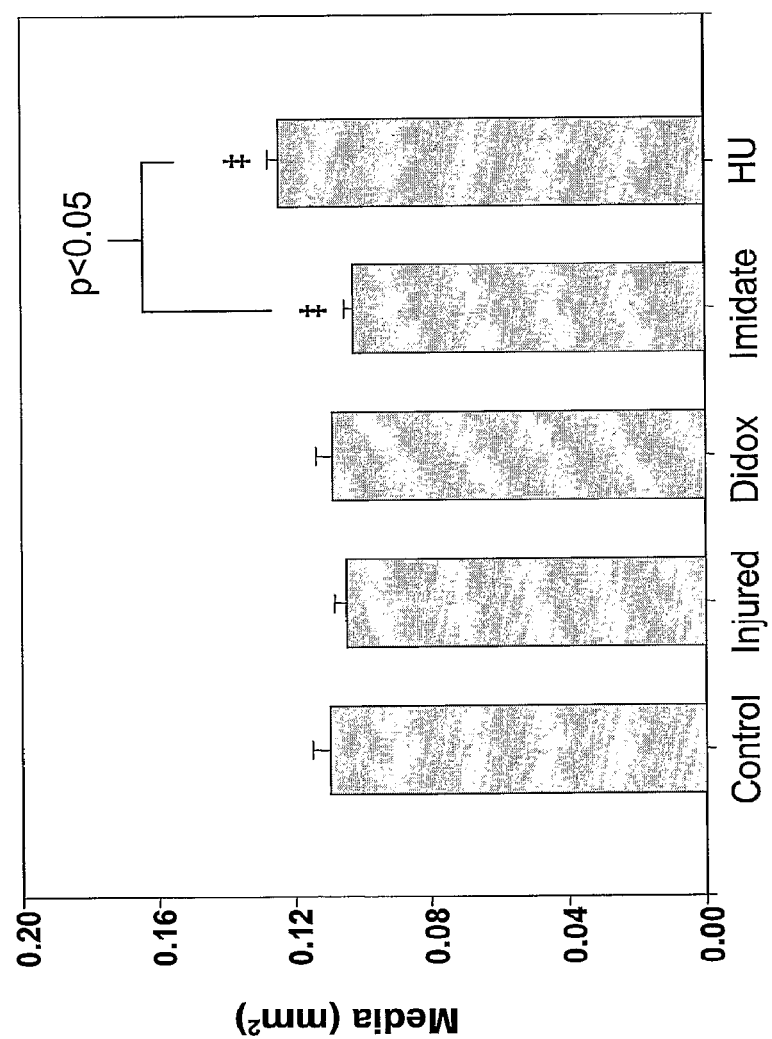
FIG. 2B compares medial wall thickness ($mm^2$).
Figure 2C:
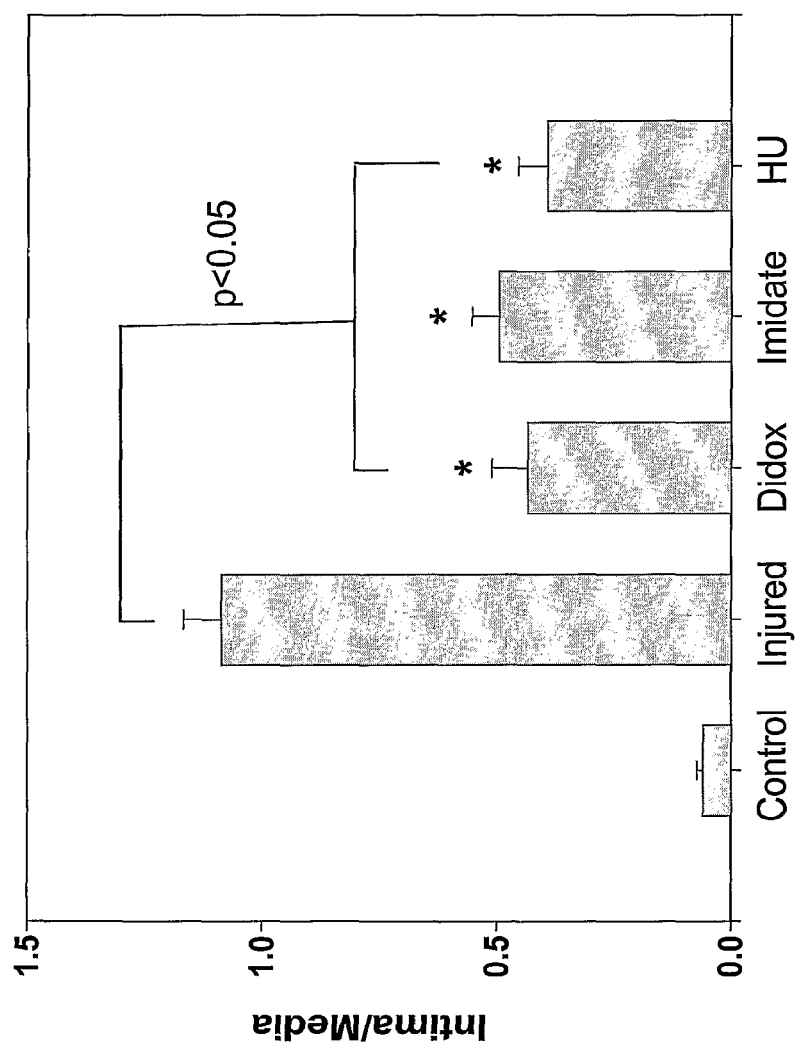
FIG. 2C compares intima to media ratio. "Control" represents the uninjured contralateral artery. "Injured" represents the ipsilateral balloon dilated artery. "Didox" represents groups that were administered Didox immediately following injury followed by daily administration for 6 days. "Imidate" represents groups that were administered Imidate immediately following injury followed by daily administration for 6 days. "HU" represents groups that were administered HU immediately following injury followed by daily administration for 6 days. The data represent the mean±SD. "*" indicates significantly different at $p<0.05$ as compared to injured (untreated). "‡" indicates significantly different at $p<0.05$ among treated groups.

At 14 days post injury the animals were sacrificed and morphometric analysis was carried out in order to asses the histopathological changes in the vessel wall (FIG. 1). Didox treatment resulted in a 62% decrease in neointimal area and a 61% decrease in intima/media ratio (FIG. 2). Imidate treated groups demonstrated a 57% decrease in neointimal area and a 55% decrease in the intima/media ratio (FIG. 2). Because Didox and Imidate possess other chemical attributes in addition to their effects on ribonucleotide reductase (Fritzer-Szekeres et al., (2000) *Exp Hematol* 28:924-930; Fritzer-Szekeres et al., (1997) *Life Sci* 61:2231-2237; Fritzer-Szekeres et al., (2002) *Biochem Pharmacol* 64:481-485; Lee et al., (1997) *Virology* 234:277-290; Inayat et al., (2002) *Cancer Biol Ther* 1:539-545) the commercially available ribonucleotide reductase inhibitor, HU (200 mg kg$^{-1}$ d$^{-1}$), was also tested. HU afforded similar vascular protective effects to those observed with Didox and Imidate, resulting in a 55% decrease in neointimal area and a 63% decrease in intima/media ratio (FIG. 2). These results indicate that ribonucleotide reducatase inhibition can modulate the remodeling process following vascular injury. However, because the remodeling process occurs over a prolonged period of time, additional studies were performed in order to determine whether the vascular protective effects observed would be mitigated over time.

Figure 3A:
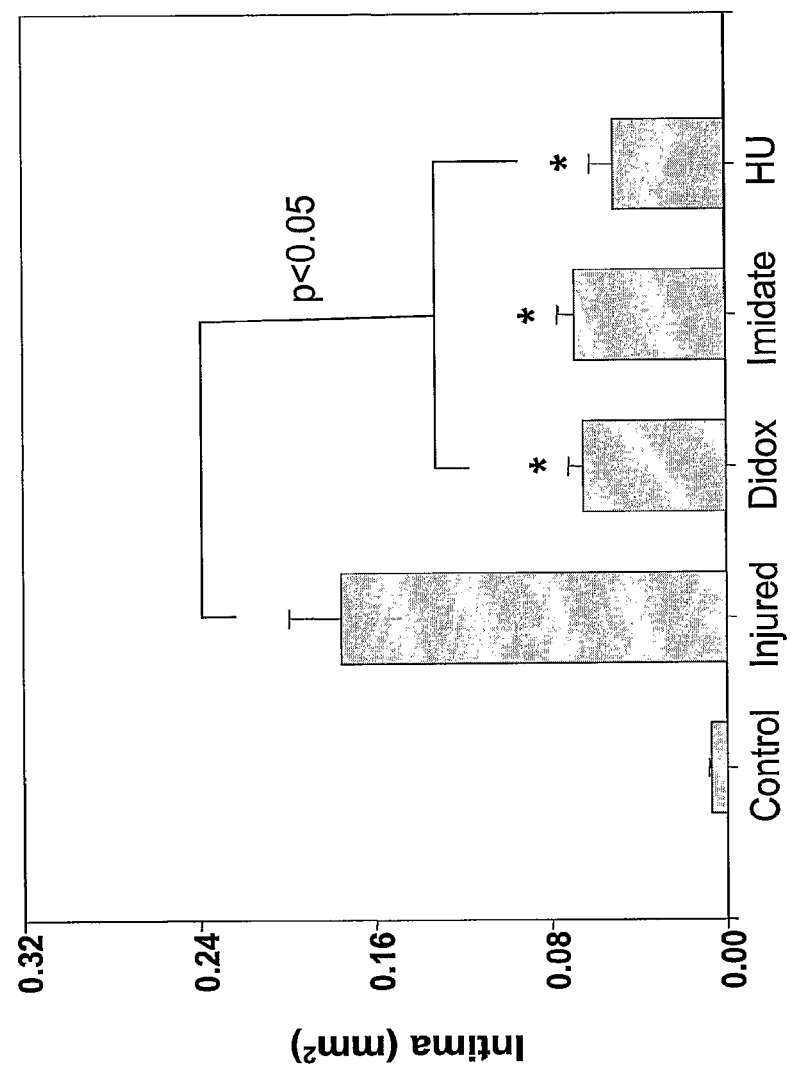
FIG. 3A compares neointima formation ($mm^2$).
Figure 3B:
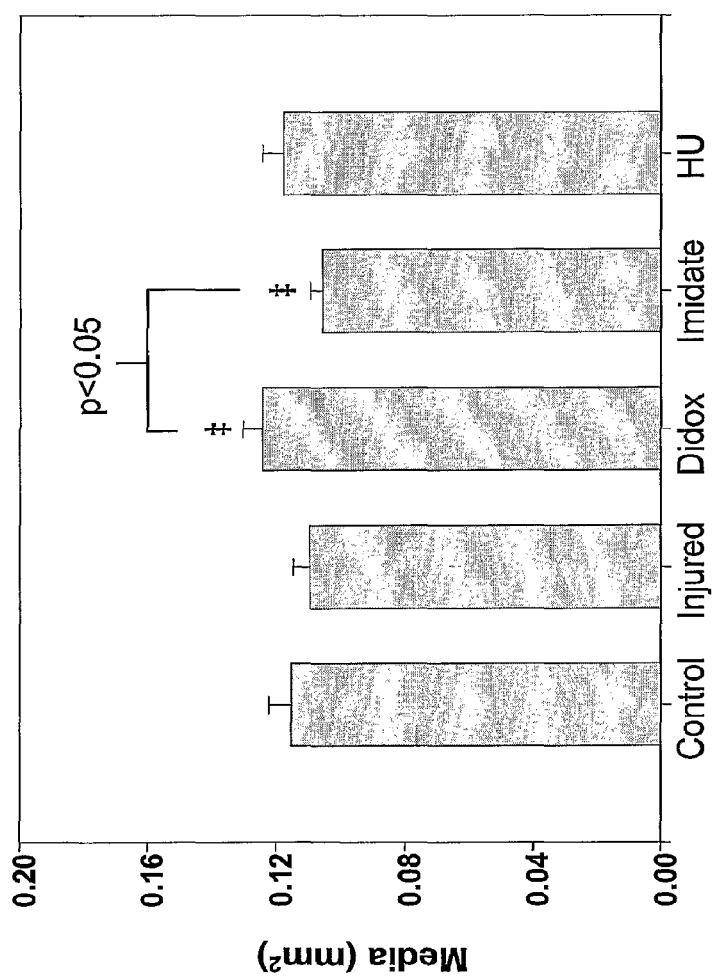
FIG. 3B compares medial wall thickness ($mm^2$).
Figure 3C:
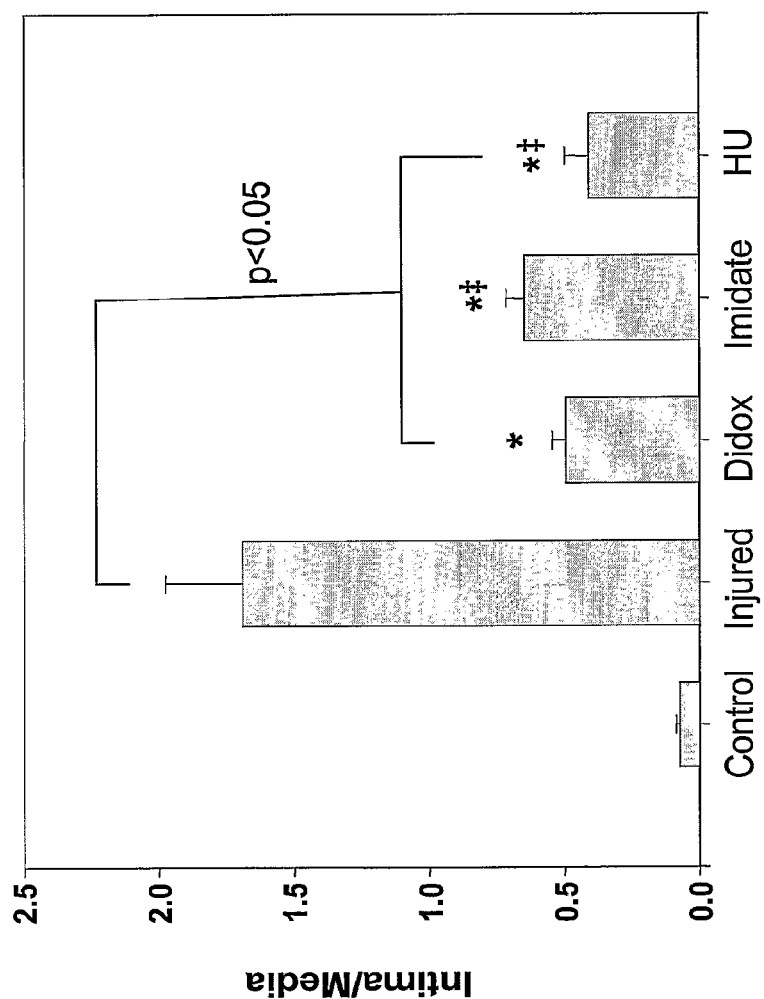
FIG. 3C compares intima to media ratio. "Control" represents the uninjured contralateral artery. "Injured" represents the ipsilateral balloon dilated artery. "Didox" represents groups that were administered Didox immediately following injury followed by daily administration for 6 days. "Imidate" represents groups that were administered Imidate immediately following injury followed by daily administration for 6 days. "HU" represents groups that were administered HU immediately following injury followed by daily administration for 6 days. The data represent the mean±SD. "*" indicates significantly different at $p<0.05$ as compared to injured (untreated). "‡" indicates significantly different at $p<0.05$ among treated groups.

To further investigate long-term efficacy of the one week dosing regimen, the duration of the study period was increased to 6 weeks. It was found that the degree of neointimal thickening at 6 weeks post-injury was increased by 57% as compared to the 2 week study paradigm (FIG. 3). The beneficial effect of ribonucleotide reductase inhibition persisted over the long term. Each compound (200 mg kg$^{-1}$ d$^{-1}$) was given i.p. for a period of 7 days followed by a 5 week recovery period. At the end of the 6 week period, the Didox treated group exhibited a 64% decrease in neointimal area and a 71% decrease in intima/media ratio (FIG. 3). Similarly, Imidate offered a 61% reduction in neointimal area and a 62% reduction in intima/media ratio (FIG. 3). HU treatment reduced neointimal formation by 71% and decreased the intima/media ratio by 75% (FIG. 3). These results suggest that activation of ribonucleotide reductase is an early trigger in the vascular response to injury and that inhibition of this enzyme can limit the neointimal proliferation associated with restenosis.

Effects of Didox, Imidate, and HU on SMC Proliferation.

Figure 4:
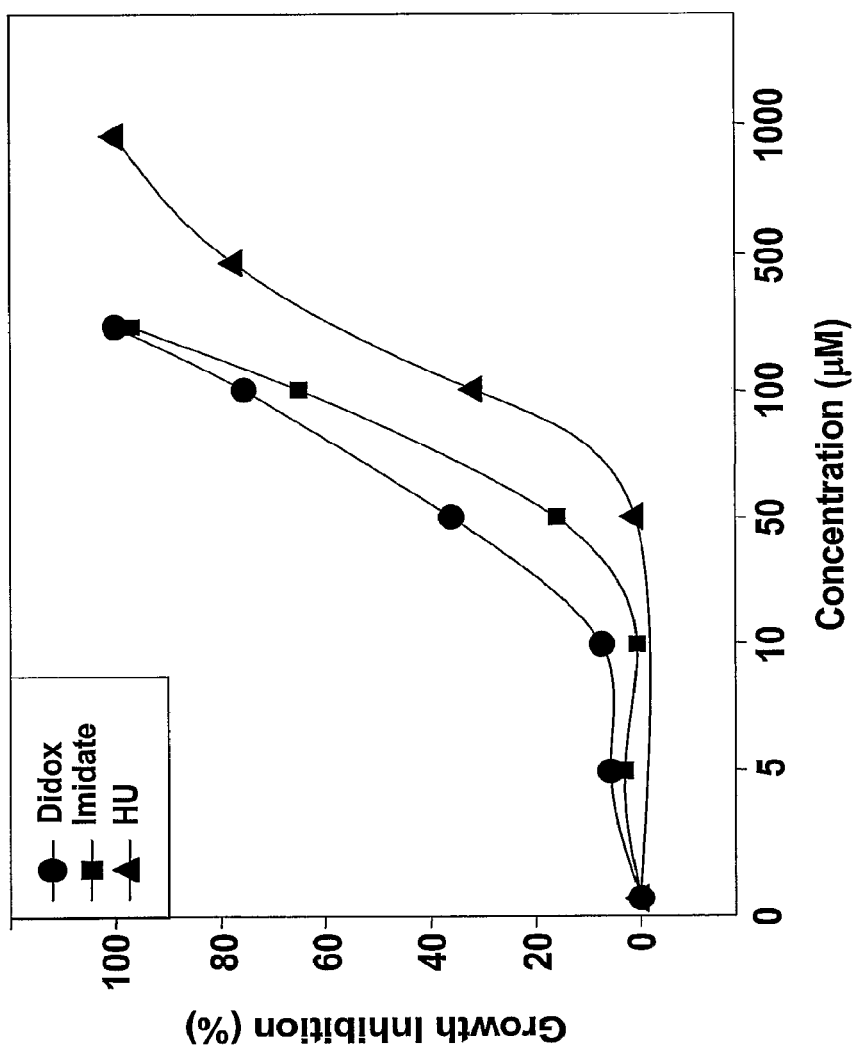
FIG. 4 is a graph showing the effect of Didox, Imidate, and HU on SMC proliferation. The graph compares percent SMC growth inhibition as a function of drug concentration ($\mu M$). Didox (0-200 $\mu M$), Imidate (0-200 $\mu M$), and HU (0-1000 $\mu M$) were added to the SMC culture during the log phase of growth and incubated for 24 hours. Cells were then counted using a flow cytometer. Values represent the mean. (n=4).

Didox, Imidate, and to a much lesser degree, HU, are known to be ribonucleotide reductase inhibitors (Elford, (1968) *Biochem Biophys Res Commun* 33:129-135; Elford et al., (1970) *J Biol Chem* 245:5228-5233; Elford et al., (1979) *Cancer Res* 39:844-851). ribonucleotide reductase catalyzes the reductive conversion of ribonucleotides to deoxynucleotides. This reductive reaction is a prime target for impeding cellular proliferation, and therefore amenable to inhibiting VSMC replication, because it is a rate limiting step in the biochemical pathway leading to DNA synthesis (Elford et al., (1970) *J Biol Chem* 245:5228-5233; Elford et al., (1979) *Cancer Res* 39:844-851; Takeda and Weber, (1981) *Life Sci* 28:1007-1014; Natsumeda et al., (1985) *Cancer Res* 45:2556-2559). The ability of Didox and Imidate to inhibit ribonucleotide reductase activity has been documented with published reports demonstrating an IC$_{50}$ of 3-30 μM for this class of compounds (Elford et al., (1979) *Cancer Res* 39:844-851). These values represent a greater than 10 fold increased effectiveness over the classical ribonucleotide reductase inhibitor HU (Elford, (1968) *Biochem Biophys Res Commun* 33:129-135). Based on this evidence, experiments were performed in order to determine whether the ability of these compounds to reduce neointimal formation was due to their ability to inhibit SMC proliferation in-vitro. Therefore, the IC$_{50}$ of each compound on inhibition of smooth muscle cell growth was determined. Cells were incubated in the presence of Didox (0-200 μM), Imidate (0-200 μM), and HU (0-1000 μM) for 24 hours. Cell numbers were then counted using flow cytometry and the concentration at which cell division was inhibited by 50% (IC$_{50}$) was calculated. Didox yielded an IC$_{50}$ of 67 μM, Imidate was slightly less potent exhibiting an IC$_{50}$ of 82 μM, while HU was the least potent with an IC$_{50}$ of 266 μM (FIG. 4). These results are consistent with ribonucleotide reductase activity data and demonstrate that Didox and Imidate are 3-4 times more potent than HU at arresting cell division in vascular smooth muscle cells.

In order to further validate that the observed anti-proliferative properties afforded by these compounds was through inhibition of ribonucleotide reductase activity, the effects of these compounds on intracellular dATP pools were measured. Results demonstrated that Didox (0-200 μM), Imidate (0-200 μM), and HU (0-1000 μM) dose dependently depleted the endogenous dNTP pools with maximal reductions in dATP content of 58%, 42% and 69%, respectively (Table 2).

TABLE 2

Effects of Didox, Imidate and HU on SMC dATP pools. Didox (0-200 μM), Imidate (0-200 μM) and HU (0-1000 μM) were added to the SMC culture during the log phase of growth and incubated for 24 hours. dNTP's were extracted and samples subjected to HPLC analysis. The data are presented as pmoles dATP/107 cells and represent the mean ± SD.

| | Control | Didox (μM) | | | | | Imidate (μM) | | | | | Hydroxyurea (μM) | | | |
|---|---|---|---|---|---|---|---|---|---|---|---|---|---|---|---|
| Dose | 0 | 5 | 10 | 50 | 100 | 200 | 5 | 10 | 50 | 100 | 200 | 5 | 100 | 500 | 1000 |
| dATP levels (Pmoles/ 10$^7$ cells) | 303 | 297 | 260 | 203* | 140* | 126* | 293 | 311 | 210 | 184* | 173* | 320 | 266 | 93 | 92 |
| S.D. | 50 | 35 | 26 | 20 | 40 | 31 | 31 | 17 | 47 | 41 | 39 | 30 | 42 | 11 | 17 |

*indicates significantly different at p < 0.05 as compared to control.

The concentrations at which these drugs afford their in-vitro biological effects are well below the range of the peak plasma levels (300-400 μM) measured following Didox and Imidate infusion (200 mg kg$^{-1}$ d$^{-1}$) and would be expected to inhibit ribonucleotide reductase activity based on the published and observed K$_i$'s for these compounds (Elford et al., (1979) *Cancer Res* 39:844-851). These results indicate that part of the vascular protective effects of these compounds is due to their ability to impede SMC proliferation.

Effects of Didox, Imidate, and HU on SMC Migration.

Figure 5:
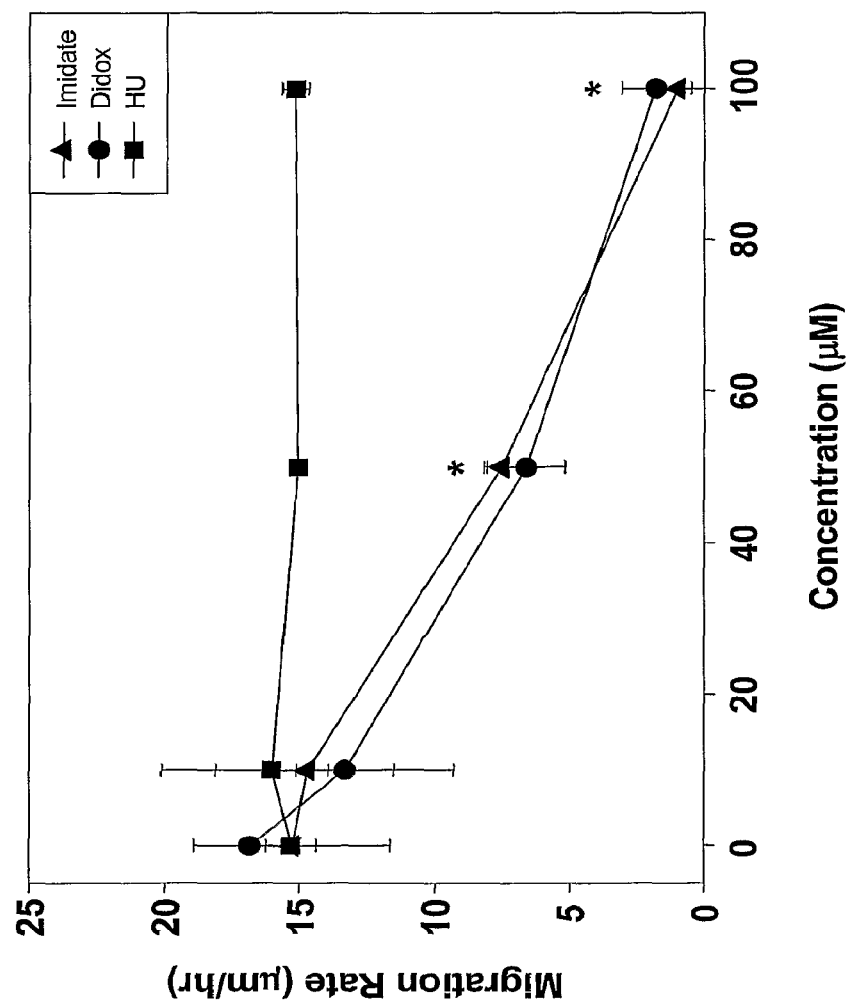
FIG. 5 is a graph showing the effects of Didox, Imidate, and HU on SMC migration. The graph compares migration rate ($\mu m/hr$) as a function of concentration ($\mu M$). Didox (0-100 $\mu M$), Imidate (0-100 $\mu M$), and HU (0-1000 $\mu M$) were added to the SMC culture in media containing 0.1% serum and 10 ng/mL platelet derived growth factor (PDGF). A wound scrape was then made and SMC migration was monitored for an additional 24 hours. The data represent the mean±SD. "*" indicates significantly different at $p<0.05$ as compared to control.

SMC migration is also a component of neointimal proliferation. Therefore, additional studies were performed in order to determine the effects of these compounds on SMC migration. Using a wound scrape assay, SMC migration studies were carried out in the presence of Didox, Imidate, and HU. VSMC's were cultured to confluence on 60 mm dishes. The cells were made quiescent by incubating in media containing 0.1% serum. Following 24 hours of serum deprivation, Didox, Imidate, and HU were added to the wells (10-1000 μM) in the presence of PDGF (10 ng/mL) and a linear wound was made across the plate. SMC migration across the wound was monitored by digital microscopy over a 24 hour period. Results from these studies demonstrated that Didox (100 μM) and Imidate (100 μM) treatment almost completely inhibited SMC migration, decreasing the migratory rate from 15.8 μM/hr in the control to 1.7 μM/hr and 0.9 μM/hr, respectively (FIG. 5). In contrast, HU (100 μM) had little effect on SMC migration, resulting in a migratory rate of 15.1 µM/hr (FIG. 4). No further inhibition was seen with HU concentrations up to 1 mM. These results demonstrate that Didox and Imidate significantly impair SMC migration. This would be expected to contribute to the vascular protective effects afforded by these drugs. However, ribonucleotide reductase inhibition appears to be the principal mechanism as the rat arterial injury data demonstrated similar efficacy with HU.

Discussion

Although PTCA and coronary artery stenting have had a tremendous impact on the treatment of coronary vascular disease, these procedures are marked by a high incidence of restenosis (Anderson et al., (1993) *J Interv Cardiol* 6:187-202; Fischman et al., (1994) *N Engl J Med* 331:496-501; Elezi et al., (1998) *Circulation* 98:1875-1880; Bennett and O'Sullivan, (2001) *Pharmacol Ther* 91:149-166; Heckenkamp et al., (2002) *J Cardiovasc Surg (Torino)* 43:349-357). This process of vessel re-narrowing is characterized by neointimal hyperplasia resulting in lumen loss and impaired vascular function. The vascular response to injury triggers a migratory and proliferative response within the smooth muscle cells resulting in intimal thickening (Noda-Heiny and Sobel, (1995) *Am J Physiol* 268:C1195-1201; Libby and Tanaka, (1997) *Frog Cardiovasc Dis* 40:97-106; Elezi et al., (1998) *Circulation* 98:1875-1880; Ward et al., (2000) *Circulation* 102:1186-1191; Bennett and O'Sullivan, (2001) *Pharmacol Ther* 91:149-166; Heckenkamp et al., (2002) *J Cardiovasc Surg (Torino)* 43:349-357; Lanza et al., (2002) *Circulation* 106:2842-2847; Segev et al., (2002) *Cardiovasc Res* 53:232-241; Bhargava et al., (2003) *Bmj* 327:274-279; Crook and Akyurek (2003) *Trends Cardiovasc Med* 13:102-106; Indolfi et al., (2003) *Trends Cardiovasc Med* 13:142-148). In this regard, emphasis has been placed on developing pharmacological therapy aimed at reducing the proliferative response. Currently, two pharmacological agents have been approved for clinical use in the treatment of post-PTCA restenosis (Drachman et al., (2000) *J Am Coll Cardiol* 36:2325-2332; Heldman et al., (2001) *Circulation* 103:2289-2295; Suzuki et al., (2001) *Circulation* 104:1188-1193). Taxol and Rapamyacin are being delivered through the use of coated coronary stents. Preliminary results suggest that these approaches offer significant protection against the restenosis process and validate the use of antiproliferative agents in the treatment of vascular proliferative disorders such as restenosis (Sousa et al., (2001) *Circulation* 103:192-195; Gershlick et al., (2004) *Circulation* 109:487-493; Stone et al., (2004) *Circulation* 109:1942-1947).

The use of ribonucleotide reductase inhibition has been demonstrated herein as a new therapeutic target in ameliorating balloon mediated restenosis injury. The biochemical attributes of this enzyme make it amenable for the treatment of proliferative disorders since inhibition of ribonucleotide reductase blocks DNA synthesis and thus cell replication. These results herein demonstrate that following balloon injury, one week of systemic administration of the ribonucleotide reductase inhibitors, Didox and Imidate, largely inhibited neointimal formation resulting in a 60% reduction in the intima/media ratio. Morphometric analysis revealed an about 60% reduction in neointimal area with no significant change in the medial area between treated and untreated groups. However, there was a small but statistically significant decrease in medial area following Imidate dosing when this cohort was compared against HU and Didox. These results indicate that Imidate can have some negative effects on smooth muscle remodeling following medial injury that result in medial wall thinning.

These disclosed in-vivo studies demonstrate that inhibition of ribonucleotide reductase limits the extent of intimal hyperplasia following mechanical injury. Also, these compounds possess a variety of chemical attributes that can contribute to their protective effects. Didox has been shown to inhibit NF-kappa B and Tissue Factor expression. In addition both Didox and Imidate compounds are potent free radical scavengers (Fritzer-Szekeres et al., (1997) *Life Sci* 61:2231-2237; Lee et al, (1997) *Virology* 234:277-290; Duilio et al., (2001) *Am J Physiol Heart Circ Physiol* 280:H2649-2657; Shet et al., (2003) *Blood* 102:2678-2683; Turchan et al., (2003) *Neurology* 60:307-314; Inayat *Cancer Biol Ther*. (2002) 1(5):539-545). Because of the myriad of effects elicited by these compounds, further experiments were carried out using the commercially available ribonucleotide reductase inhibitor, HU. Following the same dosing regimen for Didox and Imidate, HU afforded similar anti-restenotic efficacy, further supporting the observation described herein regarding the importance of ribonucleotide reductase in the vascular response to injury.

Because the vascular response to injury is a chronic process, additional studies were performed in order to assess whether the protective effects elicited by early ribonucleotide reductase inhibition are maintained throughout the remodeling period. The ribonucleotide reductase inhibitors (Didox, Imidate, and HU) were administered daily for one week and the extent of injury assessed at 6 weeks after balloon dilatation. This additional recovery time resulted in a greater than 50% increase in the intima/media ratio demonstrating the progression of the lesion over time. Interestingly, Didox and HU treatment reduced the intima/media ratio by greater than 70%, while slightly less efficacy was observed with Imidate. Moreover, the degree of protection afforded by these compounds was significantly increased when compared to the results of the two week study. This suggests that ribonucleotide reductase is an early target in the vascular response to injury and that inhibition of this enzyme affects the long term vascular remodeling associated with restenosis.

These results demonstrate that ribonucleotide reductase inhibition limits the degree of restenosis following arterial dilation injury. While not wishing to be bound by theory, it is believed that these effects are mediated through an inhibition of SMC proliferation, as this process precedes neointimal formation. Therefore, studies were performed using a cell proliferation assay. Didox, Imidate, and HU treatment resulted in arrest of cell division. Analysis of dNTP pools demonstrated a greater than 50% reduction in dATP levels further supporting that the observed effects of these drugs are mediated at least in part through the inhibition of ribonucleotide reductase. These effects were independent of any cytotoxic action these compounds may posses as flow cytometry revealed less than 3% apoptotic cells following the dosing regimes tested. In addition, prior to dNTP analysis, cells were counted and viability assessed using trypan blue exclusion. Cell viability was greater than 95% among all groups.

As previously stated, Didox and Imidate possess various chemical attributes in addition to ribonucleotide reductase inhibition, many of which can confer protection against restenosis (Fritzer-Szekeres et al., (1997) *Life Sci* 61:2231-2237; Lee et al., (1997) *Virology* 234:277-290; Duilio et al., (2001) *Am J Physiol Heart Circ Physiol* 280:H2649-2657; Shet et al., (2003) *Blood* 102:2678-2683; Turchan et al., (2003) *Neurology* 60:307-314). Among these is their ability to scavenge free radicals, which can modulate SMC migration, a component of neointimal proliferation (Duilio et al., (2001) *Am J Physiol Heart Circ Physiol* 280:H2649-265; Turchan et al., (2003) *Neurology* 60:307-314). Therefore, the effects of Didox and Imidate were tested on SMC proliferation using a wound scrape assay. Results demonstrated that both compounds almost completely inhibited SMC migration. This indicates that inhibition of SMC proliferation can contribute to the protection afforded by these compounds. Similarly, a number of studies have demonstrated that HU, when oxidized, can release NO. (Stolze and Nohl, (1990) *Biochem Pharmacol* 40:799-802; Pacelli et al., (1996) *Lancet* 347:900). Because NO has been shown to inhibit cell migration, it was tested whether HU possesses anti-migratory properties which could be involved in its anti-restenotic effects (Sarkar et al., (1997) *Am J Physiol* 272:H1810-1818; Sarkar and Webb, (1998) *J Vasc Res* 35:135-142). HU at concentrations up to 1 mM had no effect on SMC migration. This observation indicates that inhibition of ribonucleotide reductase is the principal mechanism through which these compounds afford their protection as similar efficacy was seen with all compounds. However, if the in-vivo results are interpreted on a molar basis, HU (2.6 mmoles $kg^{-1}$ $d^{-1}$) doses are 2-3 fold higher than that of Didox (1.2 mmoles $kg^{-1}$ $d^{-1}$) and Imidate (0.9 mmoles $kg^{-1}$ $d^{-1}$) and suggests that the effects of Didox and Imidate on SMC migration can contribute to the vascular protective effects observed with these two compounds.

Taken together, the in-vivo and in-vitro data demonstrate that activation of ribonucleotide reductase is an early component in the proliferative response associated with vascular injury and that inhibition of this enzyme can reduce the vascular pathology associated with restenosis injury. Although the incidence of restenosis has markedly decreased with the advent of drug coated stents, restenosis still occurs in up to 20% of patients within the first year while results on late lumen loss are still being gathered (Drachman et al., (2000). *J Am Coll Cardiol* 36:2325-2332; Heldman et al., (2001) *Circulation* 103:2289-2295; Grube et al., (2003) *Circulation* 107:38-42; Kastrati et al., (2005) *JAMA* 293:165-171; Kim et al., (2005) *Heart* 91:e15). In addition, because the use of coated stents may increase the risk of thrombosis there is a need for agents which can be administered systemically with or without stents in patients at high risk for thrombotic events (Morice, (2005) *JACC* 45). Inhibition of ribonucleotide reductase can be a pathway that can be therapeutically targeted through either local or systemic delivery based on the low toxicity associated with current ribonucleotide reductase inhibitor therapy using HU. Additionally, the data disclosed herein suggest that ribonucleotide reductase is an early target in the restenosis process and as such, early pharmacological intervention can preclude chronic therapy and its associated adverse side effects. It is believed that these observations have therapeutic potential and implicate ribonucleotide reductase as a promising therapeutic target in the treatment of vascular proliferative disorders.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

REFERENCES

Anderson H V, Vignale S J, Benedict C R and Willerson J T (1993) Restenosis after coronary angioplasty. *J Interv Cardiol* 6:187-202.

Bauters C and Isner J M (1997) The biology of restenosis. *Prog Cardiovasc Dis* 40:107-116.

Bennett M R and O'Sullivan M (2001) Mechanisms of angioplasty and stent restenosis: implications for design of rational therapy. *Pharmacol Ther* 91:149-166.

Bhargava B, Karthikeyan G, Abizaid A S and Mehran R (2003) New approaches to preventing restenosis. *Bmj* 327:274-279.

Crook M F and Akyurek L M (2003) Gene transfer strategies to inhibit neointima formation. *Trends Cardiovasc Med* 13:102-106.

Drachman D E, Edelman E R, Seifert P, Groothuis A R, Bornstein D A, Kamath K R, Palasis M, Yang D, Nott S H and Rogers C (2000) Neointimal thickening after stent delivery of paclitaxel: change in composition and arrest of growth over six months. *J Am Coll Cardiol* 36:2325-2332.

Duilio C, Ambrosio G, Kuppusamy P, DiPaula A, Becker L C and Zweier J L (2001) Neutrophils are primary source of O2 radicals during reperfusion after prolonged myocardial ischemia. *Am J Physiol Heart Circ Physiol* 280:H2649-2657.

Elezi S, Kastrati A, Neumann F J, Hadamitzky M, Dirschinger J and Schomig A (1998) Vessel size and long-term outcome after coronary stent placement. *Circulation* 98:1875-1880.

Elford H L (1968) Effect of hydroxyurea on ribonucleotide reductase. *Biochem Biophys Res Commun* 33:129-135.

Elford H L, Freese M, Passamani E and Morris H P (1970) Ribonucleotide reductase and cell proliferation. I. Variations of ribonucleotide reductase activity with tumor growth rate in a series of rat hepatomas. *J Biol Chem* 245:5228-5233.

Elford H L, Wampler G L and van't Riet B (1979) New ribonucleotide reductase inhibitors with antineoplastic activity. *Cancer Res* 39:844-851.

Epstein S E, Siegall C B, Biro S, Fu Y M, FitzGerald D and Pastan I (1991) Cytotoxic effects of a recombinant chimeric toxin on rapidly proliferating vascular smooth muscle cells. *Circulation* 84:778-787.

Farb A, Weber D K, Kolodgie F D, Burke A P and Virmani R (2002) Morphological predictors of restenosis after coronary stenting in humans. *Circulation* 105:2974-2980.

Fischman D L, Leon M B, Baim D S, Schatz R A, Savage M P, Penn I, Detre K, Veltri L, Ricci D, Nobuyoshi M and et al. (1994) A randomized comparison of coronary-stent placement and balloon angioplasty in the treatment of coronary artery disease. Stent Restenosis Study Investigators. *N Engl J Med* 331:496-501.

Fritzer-Szekeres M, Grusch M, Luxbacher C, Horvath S, Krupitza G, Elford H L and Szekeres T (2000) Trimidox, an inhibitor of ribonucleotide reductase, induces apoptosis and activates caspases in HL-60 promyelocytic leukemia cells. *Exp Hematol* 28:924-930.

Fritzer-Szekeres M, Novotny L, Vachalkova A, Findenig G, Elford H L and Szekeres T (1997) Iron binding capacity of didox (3,4-dihydroxybenzohydroxamic acid) and amidox (3,4-dihydroxybenzamidoxime) new inhibitors of the enzyme ribonucleotide reductase. *Life Sci* 61:2231-2237.

Fritzer-Szekeres M, Salmon A, Grusch M, Horvath Z, Hochtl T, Steinbrugger R, Jager W, Krupitza G, Elford H L and Szekeres T (2002) Trimidox, an inhibitor of ribonucleotide reductase, synergistically enhances the inhibition of colony formation by Ara-C in HL-60 human promyelocytic leukemia cells. *Biochem Pharmacol* 64:481-485.

Gershlick A, De Scheerder I, Chevalier B, Stephens-Lloyd A, Camenzind E, Vrints C, Reifart N, Missault L, Goy J J, Brinker J A, Raizner A E, Urban P and Heldman A W (2004) Inhibition of restenosis with a paclitaxel-eluting, polymer-free coronary stent: the European evaLUation of pacliTaxel Eluting Stent (ELUTES) trial. *Circulation* 109: 487-493. Epub 2004 January 2026.

Goldschmidt-Clermont P J and Moldovan L (1999) Stress, superoxide, and signal transduction. *Gene Expr* 7:255-260.

Grube E, Silber S, Hauptmann K E, Mueller R, Buellesfeld L, Gerckens U and Russell M E (2003) TAXUS I: six- and twelve-month results from a randomized, double-blind trial on a slow-release paclitaxel-eluting stent for de novo coronary lesions. *Circulation* 107:38-42.

Gupta C and Yaffe S J (1982) Phenobarbital-induced alterations in the sexual differentiation of the female rat: reversal by hydroxyurea and cycloheximide. *Pediatr Pharmacol (New York)* 2:85-91.

Heckenkamp J, Gawenda M and Brunkwall J (2002) Vascular restenosis. Basic science and clinical implications. *J Cardiovasc Surg (Torino)* 43:349-357.

Heldman A W, Cheng L, Jenkins G M, Heller P F, Kim D W, Ware M, Jr., Nater C, Hruban R H, Rezai B, Abella B S, Bunge K E, Kinsella J L, Sollott S J, Lakatta E G, Brinker J A, Hunter W L and Froehlich J P (2001) Paclitaxel stent coating inhibits neointimal hyperplasia at 4 weeks in a porcine model of coronary restenosis. *Circulation* 103: 2289-2295.

Horvath Z, Hochtl T, Bauer W, Fritzer-Szekeres M, Elford H L, Szekeres T, Tihan T (2004) Synergistic cytotoxicity of the ribonucleotide reductase inhibitor didox (3,4-dihydroxy-benzohydroxamic acid) and the alkylating agent carmustine (BCNU) in 9 L rat gliosarcoma cells and DAOY human medulloblastoma cells. *Cancer Chemother Pharmacol.* 54(2):139-45.

Inayat M S, Chendil D, Mohiuddin M, Elford H L, Gallicchio V S and Ahmed M M (2002) Didox (a novel ribonucleotide reductase inhibitor) overcomes Bcl-2 mediated radiation resistance in prostate cancer cell line PC-3. *Cancer Biol Ther* 1:539-545.

Indolfi C, Mongiardo A, Curcio A and Torella D (2003) Molecular mechanisms of in-stent restenosis and approach to therapy with eluting stents. *Trends Cardiovasc Med* 13:142-148.

Kastrati A, Mehilli J, von Beckerath N, Dibra A, Hausleiter J, Pache J, Schuhlen H, Schmitt C, Dirschinger J and Schomig A (2005) Sirolimus-eluting stent or paclitaxel-eluting stent vs balloon angioplasty for prevention of recurrences in patients with coronary in-stent restenosis: a randomized controlled trial. *Jama* 293:165-171.

Kim J W, Park C G, Seo H S and Oh D J (2005) Delayed severe multivessel spasm and aborted sudden death after Taxus stent implantation. *Heart* 91:e15.

Lanza G M, Yu X, Winter P M, Abendschein D R, Karukstis K K, Scott M J, Chinen L K, Fuhrhop R W, Scherrer D E and Wickline S A (2002) Targeted antiproliferative drug delivery to vascular smooth muscle cells with a magnetic resonance imaging nanoparticle contrast agent: implications for rational therapy of restenosis. *Circulation* 106: 2842-2847.

Lee R, Beauparlant P, Elford H, Ponka P and Hiscott J (1997) Selective inhibition of 1 kappaB alpha phosphorylation and HIV-1 LTR-directed gene expression by novel antioxidant compounds. *Virology* 234:277-290.

Libby P and Tanaka H (1997) The molecular bases of restenosis. *Prog Cardiovasc Dis* 40:97-106.

Mayhew C N, Phillips J D, Cibull M L, Elford H L and Gallicchio V S (2002) Short-term treatment with novel ribonucleotide reductase inhibitors Trimidox and Didox reverses late-stage murine retrovirus-induced lymphoproliferative disease with less bone marrow toxicity than hydroxyurea. *Antivir Chem Chemother* 13:305-314.

Mayhew C N, Phillips J D, Greenberg R N, Birch N J, Elford H L and Gallicchio V S (1999) In vivo and in vitro comparison of the short-term hematopoietic toxicity between hydroxyurea and trimidox or didox, novel ribonucleotide reductase inhibitors with potential anti-HIV-1 activity. *Stem Cells* 17:345-356.

Morice M (2005) Eight-Month Outcome of the Reality Study: A Prospective Randomized Multi-Center Head-to-Head Comparison of the Sirolimus-Eluting Stent (Cypher) and the Paclitaxel-Eluting Stent (Taxus). *JACC* 45.

Natsumeda Y, Lui M S, Emrani J, Faderan M A, Reardon M A, Eble J N, Glover J L and Weber G (1985) Purine enzymology of human colon carcinomas. *Cancer Res* 45:2556-2559.

Noda-Heiny H and Sobel B E (1995) Vascular smooth muscle cell migration mediated by thrombin and urokinase receptor. *Am J Physiol* 268:C1195-1201.

Pacelli R, Taira J, Cook J A, Wink D A and Krishna M C (1996) Hydroxyurea reacts with heme proteins to generate nitric oxide. *Lancet* 347:900.

Sarkar R, Gordon D, Stanley J C and Webb R C (1997) Cell cycle effects of nitric oxide on vascular smooth muscle cells. *Am J Physiol* 272:H1810-1818.

Sarkar R and Webb R C (1998) Does nitric oxide regulate smooth muscle cell proliferation? A critical appraisal. *J Vasc Res* 35:135-142.

Segev A, Aviezer D, Safran M, Gross Z and Yayon A (2002) Inhibition of vascular smooth muscle cell proliferation by a novel fibroblast growth factor receptor antagonist. *Cardiovasc Res* 53:232-241.

Shet A S, Aras O, Gupta K, Hass M J, Rausch D J, Saba N, Koopmeiners L, Key N S and Hebbel R P (2003) Sickle blood contains tissue factor-positive microparticles derived from endothelial cells and monocytes. *Blood* 102: 2678-2683. Epub 2003 June 2612.

Sousa J E, Costa M A, Abizaid A, Abizaid A S, Feres F, Pinto I M, Seixas A C, Staico R, Mattos L A, Sousa A G, Falotico R, Jaeger J, Popma J J and Serruys P W (2001) Lack of neointimal proliferation after implantation of sirolimus-coated stents in human coronary arteries: a quantitative coronary angiography and three-dimensional intravascular ultrasound study. *Circulation* 103:192-195.

Stolze K and Nohl H (1990) EPR studies on the oxidation of hydroxyurea to paramagnetic compounds by oxyhemoglobin. *Biochem Pharmacol* 40:799-802.

Stone G W, Ellis S G, Cox D A, Hermiller J, O'Shaughnessy C, Mann J T, Turco M, Caputo R, Bergin P, Greenberg J, Popma J J and Russell M E (2004) One-year clinical results with the slow-release, polymer-based, paclitaxel-eluting TAXUS stent: the TAXUS-IV trial. *Circulation* 109:1942-1947. Epub 2004 April 1912.

Suzuki T, Kopia G, Hayashi S, Bailey L R, Llanos G, Wilensky R, Klugherz B D, Papandreou G, Narayan P, Leon M B, Yeung A C, Tio F, Tsao P S, Falotico R and Carter A J (2001) Stent-based delivery of sirolimus reduces neointimal formation in a porcine coronary model. *Circulation* 104:1188-1193.

Takeda E and Weber G (1981) Role of ribonucleotide reductase in expression in the neoplastic program. *Life Sci* 28:1007-1014.

Tanaka H, Arakawa H, Yamaguchi T, Shiraishi K, Fukuda S, Matsui K, Takei Y and Nakamura Y (2000) A ribonucleotide reductase gene involved in a p53-dependent cell-cycle checkpoint for DNA damage. *Nature* 404:42-49.

Turchan J, Pocernich C B, Gairola C, Chauhan A, Schifitto G, Butterfield D A, Buch S, Narayan O, Sinai A, Geiger J, Berger J R, Elford H and Nath A (2003) Oxidative stress in HIV demented patients and protection ex vivo with novel antioxidants. *Neurology* 60:307-314.

Ueda M, Becker A E, Naruko T and Kojima A (1995) Smooth muscle cell de-differentiation is a fundamental change preceding wound healing after percutaneous transluminal coronary angioplasty in humans. *Coron Artery Dis* 6:71-81.

Vaughan W P, Holm C and Cordel K (1989) Hydroxyurea potentiation of the antineoplastic activity of cyclophosphamide and 4'-(9-acridinylamino)methanesulfon-M-anisidide (AMSA) in the brown Norway rat myelocytic leukemia model. *Cancer Chemother Pharmacol* 23:26-30.

Ward M R, Pasterkamp G, Yeung A C and Borst C (2000) Arterial remodeling. Mechanisms and clinical implications. *Circulation* 102:1186-1191.

What is claimed is:

1. A method of treating or reducing the likelihood of restenosis or a vascular injury in a subject in need thereof, comprising administering to said subject in need thereof a composition that comprises an effective amount of a compound having Formula I:

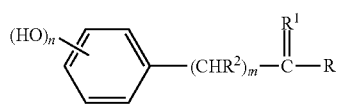

wherein n is from 2 to 5, m is 0 or 1, R is $NH_2$, NHOH, $OC_{1-3}$ alkyl, or O-phenyl, $R^1$ is O, NH, NOH, S, or SH, and $R^2$ is H, OH, SH, or $NH_2$, or a pharmaceutically acceptable salt or ester thereof, or an acylated phenol derivative thereof wherein said subject in need thereof is a subject who has restenosis or a vascular injury, or a subject who is undergoing or has undergone a vascular procedure or event wherein said subject has experienced one or more of the following: a vascular procedure that comprises angioplasty, a vascular procedure that comprises transplant surgery, a vascular procedure that comprises a vein graft or a coronary by-pass graft, a vascular procedure that comprises a percutaneous transluminal vascular intervention (PTVI), a vascular procedure that comprises intravascular device implantation or carotid endarderectomy, or a vascular procedure that comprises insertion of at least one vascular stent.

2. The method of claim 1, wherein the subject has experienced a traumatic vascular event.

3. The method of claim 1, wherein in is 1 and $R^2$ is H or OH.

4. The method of claim 1, wherein m is 0, R is NHOH, and $R^1$ is O.

5. The method of claim 1, wherein R is $NH_2$ and $R^1$ is NH.

6. The method of claim 1, wherein R is NHOH and $R^1$ is NH.

7. The method of claim 1, wherein R is NHOH and $R^1$ is NOH.

8. The method of claim 1, wherein R is $OC_{1-3}$ alkyl or O-phenyl and $R^1$ is NH.

9. The method of claim 1, wherein R is $OC_{1-3}$ alkyl.

10. The method according to claim 1, wherein the compound is selected from the group consisting of:

i)

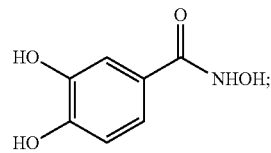

ii) 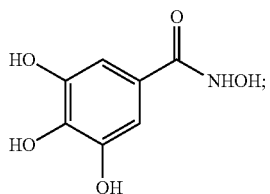

iii) 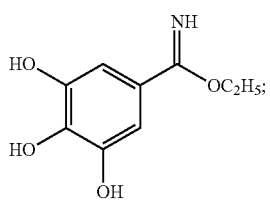

iv) 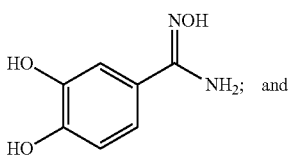

v) 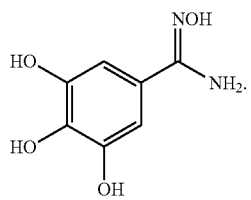

11. The method of claim 1, further comprising determining the degree of restenosis in the subject after administering the composition.

12. The method of claim 1, wherein the subject in need thereof has restenosis.

13. The method of claim 1, wherein the subject in need thereof has a vascular injury and the vascular injury is characterized by vascular injury dependent vascular smooth muscle cell migration, vascular injury dependent vascular smooth muscle cell proliferation, vascular injury dependent inflammatory activity characterized by the presence of increased inflammatory cytokines, and up-regulation of tissue factor.

14. The method of claim 1, wherein the vascular injury is caused by arteriosclerosis or procedures to treat arteriosclerosis.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
ggctaaatcg ctccaccaag                                              20

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Thr Leu Asp Ala Asp Phe
1               5
```